(12) United States Patent
Kazama

(10) Patent No.: US 9,170,185 B2
(45) Date of Patent: Oct. 27, 2015

(54) COMPUTER-READABLE RECORDING MEDIUM, SIMULATION METHOD, AND SIMULATION DEVICE

(71) Applicant: FUJITSU LIMITED, Kawasaki-shi, Kanagawa (JP)

(72) Inventor: Masaki Kazama, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/467,703

(22) Filed: Aug. 25, 2014

(65) Prior Publication Data

US 2014/0365145 A1   Dec. 11, 2014

Related U.S. Application Data

(63) Continuation of application No. PCT/JP2012/055697, filed on Mar. 6, 2012.

(51) Int. Cl.
G01N 13/00 (2006.01)
G01N 19/02 (2006.01)
G06F 17/50 (2006.01)
G01N 13/02 (2006.01)

(52) U.S. Cl.
CPC ............ *G01N 13/00* (2013.01); *G06F 17/5009* (2013.01); *G01N 13/02* (2013.01); *G01N 19/02* (2013.01); *G06F 17/50* (2013.01); *G06F 2217/16* (2013.01)

(58) Field of Classification Search
CPC . G06F 17/5009; G06F 2217/16; G06F 17/50; G01N 13/00; G01N 2013/003; G01N 13/02; G01N 19/02

USPC .......................................................... 702/50
See application file for complete search history.

(56) References Cited

U.S. PATENT DOCUMENTS 7,389,188 B2 *   6/2008  Toda et al. ....................... 702/50
2003/0145860 A1 *  8/2003  Johnson ................... 128/207.15
2004/0210429 A1   10/2004  Yu et al.

FOREIGN PATENT DOCUMENTS

JP        10-15479      1/1998
JP        10-185755     7/1998
JP        2008-111675   5/2008

OTHER PUBLICATIONS

Extended European Search Report dated Nov. 3, 2014 for corresponding European Patent Application No. 12870651.2, 6 pages.
Wrobleswski et al., "Modeling Incompressible Fluids by Means of the SPH Method: Surface Tension and Viscosity", Jun. 25, 2008, Computational Science A ICCS 2008; [Lecture Notes in Computer Science], pp. 600-609, XP019090537.

(Continued)

*Primary Examiner* — Toan Le
*Assistant Examiner* — Lynda Dinh
(74) *Attorney, Agent, or Firm* — Fujitsu Patent Center

(57) ABSTRACT

A simulation program, simulation method, or simulation device simulates the temporal shape change in a fluid. The simulation program, simulation method, and simulation device are characterized in that with respect to a fluid model representing the fluid as a collection of particles, a surface tension of an interface against another phase which is different from the phase of the fluid is calculated using a function to calculate a surface energy of the interface, and the shape change in the fluid is calculated on the basis of the calculated surface tension.

5 Claims, 20 Drawing Sheets

(56) References Cited

OTHER PUBLICATIONS

Liao, Q. et al., "Numerical simulations of the equilibrium shape of liquid droplets on gradient surfaces", Applied Thermal Engineering, vol. 29, No. 2-3, Feb. 1, 2009, pp. 372-379, XP025648353, [retrieved on Mar. 13, 2008].

Adami, S. et al., "A new surface-tension formulation for multi-phase SPH using a reproducing divergence approximation", Journal of Computational Physics, vol. 229, No. 13, Jul. 1, 2010, pp. 5011-5021, XP055149181.

X. Y. Hu et al., "A multi-phase SPH method for macroscopic and mesoscopic flows", Journal of Computational Physics (May 12, 2005) (26 pages).

T. Hongo et al., "Modeling of Surface Tension Acting on Gas-Liquid Interface in Three-Dimensional Incompressible SPH Computation", (The 23rd Numerical Fluid Dynamics Symposium), A8-5 (2009) (1 page) English Abstract.

M. Agawa et al., "Incompressible SPH Simulation of Fluid Flowing Down an Inclined Plane", (The 23rd Numerical Fluid Dynamics Symposium), A9-4 (2009) (5 pages), English Abstract.

N. Nishio et al., "SPH Simulations of Droplet Impact onto a Liquid Surface", The Japan Society of Mechanical Engineers, 20th Computational Mechanics Division Conference Koen Ronbunshu, (Nov. 26, 2007) No. 7-36, pp. 659-660 (4 pages), English Abstract.

International Search Report of PCT/JP2012/055697 mailed on Apr. 17, 2012 (2 pages).

Notification of Transmittal of Translation of The International Preliminary Report on Patentability (Form PCT/IB/338, Form PCT/IB/373 & Form PCT/ISA/237), PCT/JP2012/055697, 6 pages, mailed Sep. 18, 2014.

E. Ishii et al., "Study of Wall-adhesion Model using Inter-Particle Force in Particle Method", JSME 24th Computational Mechanics Conference (Oct. 2011), No. 11-3, pp. 105-107 (11 pages). Partial English Translation.

N. Nishio et al., "SPH Simulations of Droplet Impact onto a Liquid Surface", The Japan Society of Mechanical Engineers, 20th Computational Mechanics Division Conference Koen Ronbunshu, (Nov. 26, 2007) No. 7-36, pp. 659-660 (5 pages).

Y. Yamaguchi, "SPH", The Molecular Simulation Society of Japan, vol. 13, No. 1 (Jan. 2011), pp. 23-27 (7 pages). Partial English Translation.

Extended European Search Report dated Apr. 16, 2013 for corresponding European Application No. 12194785.7, 5 pages.

Zhang, Mingyu et al: "Simulation of surface tension in 2D and 3D with smoothed particle hydrodynamics method", Journal of Computational Physics, London, GB, vol. 229, No. 19, Sep. 20, 2010, pp. 7238-7259, XP027184313.

Omata, Seiro et al., "Variational approach to evolutionary free boundary problems", Nonlinear Analysis: Theory, Methods & Applications, vol. 71, No. 12, Dec. 1, 2009, pp. e1547-e1552, XP055058720.

Nomura, Katsuya et al, "Numerical Analysis of Droplet Breakup Behavior using Particle Method", Journal of Nuclear Science and Technology, vol. 38, No. 12, pp. 1057-1064, Dec. 2001.

Liu, Moubin et al, "Dissipative particle dynamics simulation of pore-scale multiphase fluid flow", Water Resources Research, vol. 43, pp. 1-14, W04411, doi:10.1029/2006WR004856, 2007.

Lafaurie, Bruno, "Modeling Merging and Fragmentation in Multiphase Flows with Surfer", Journal of Computational Physics, vol. 113, pp. 134-147, 1994.

U.S. Final Office Action dated Jul. 2, 2015 for related U.S. Appl. No. 13/688,295, 24 pages.

Zhang, Y. et al., "A Deformable Surface Model for Real-Time Water Drop Animation", IEEE Transactions on Visualization and Computer Graphics, vol. 18, No. 8, Aug. 25, 2011, pp. 1281-1289.

\* cited by examiner

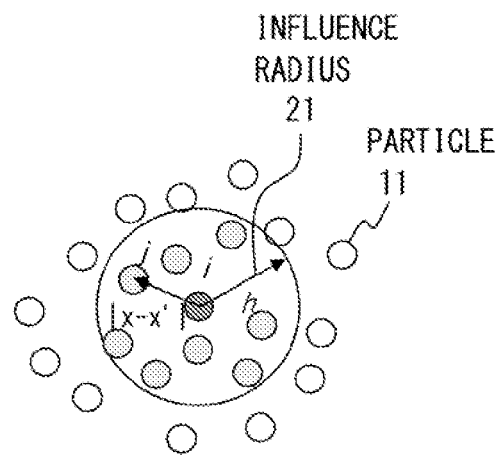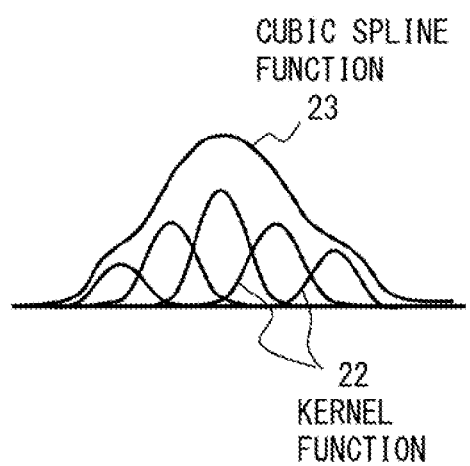
FIG. 2A  FIG. 2B
FIG. 2

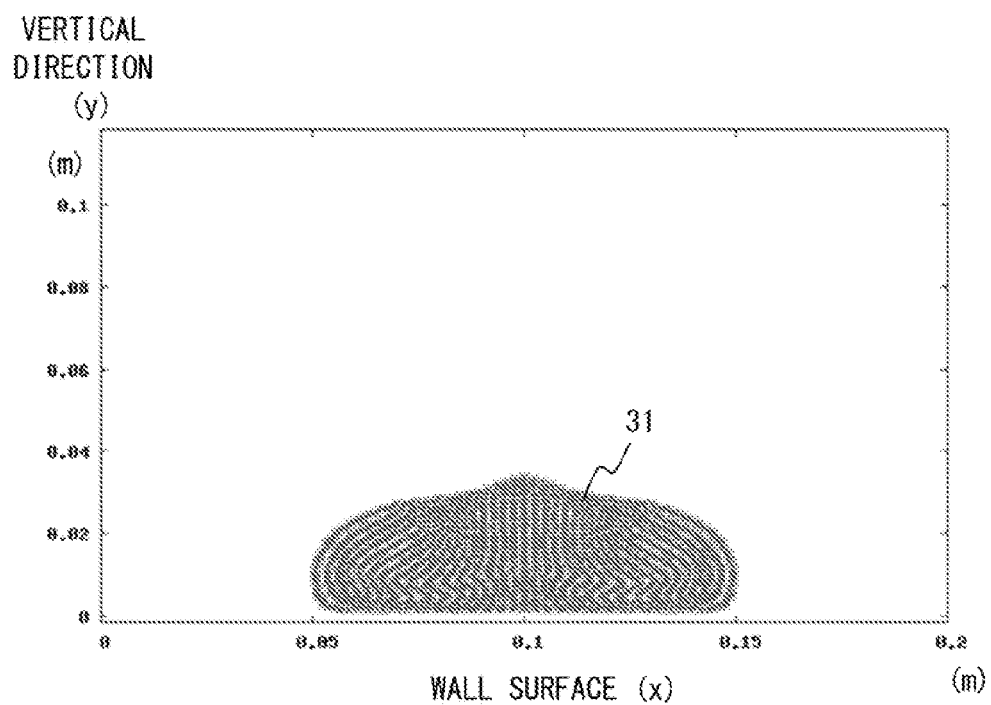
F I G. 5

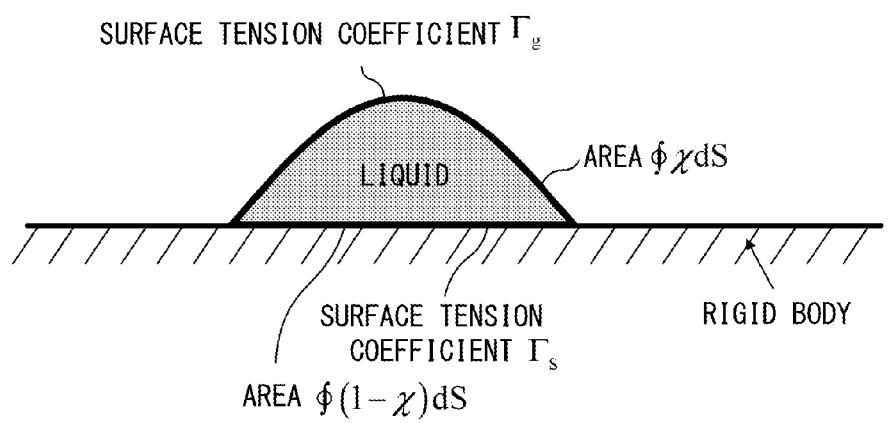
F I G. 8

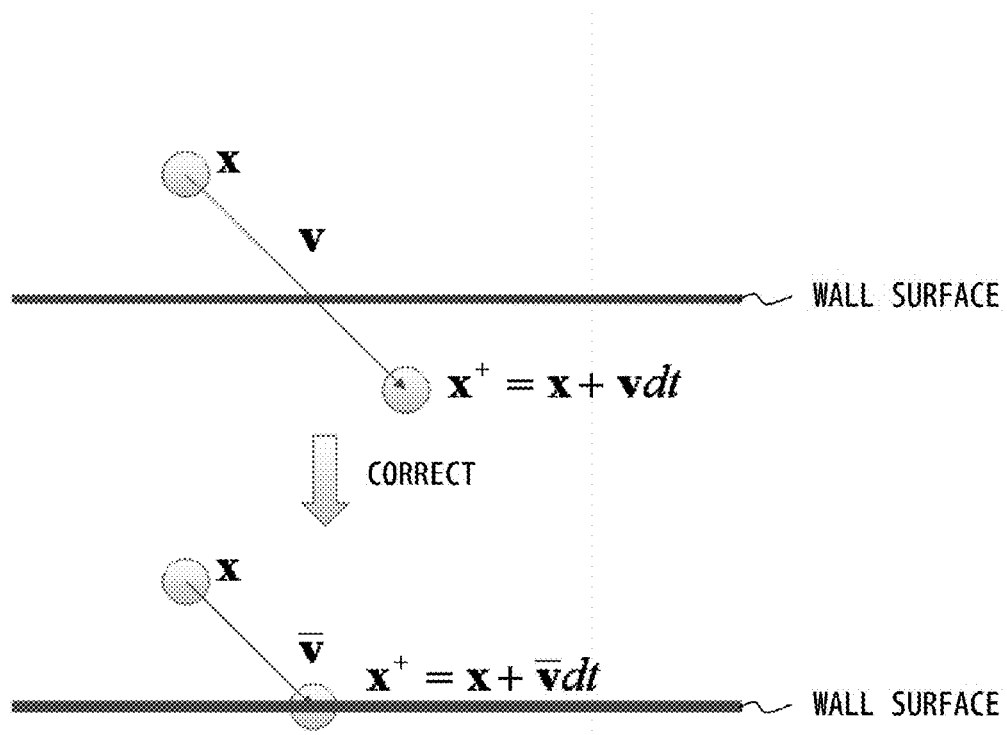
F I G. 1 2

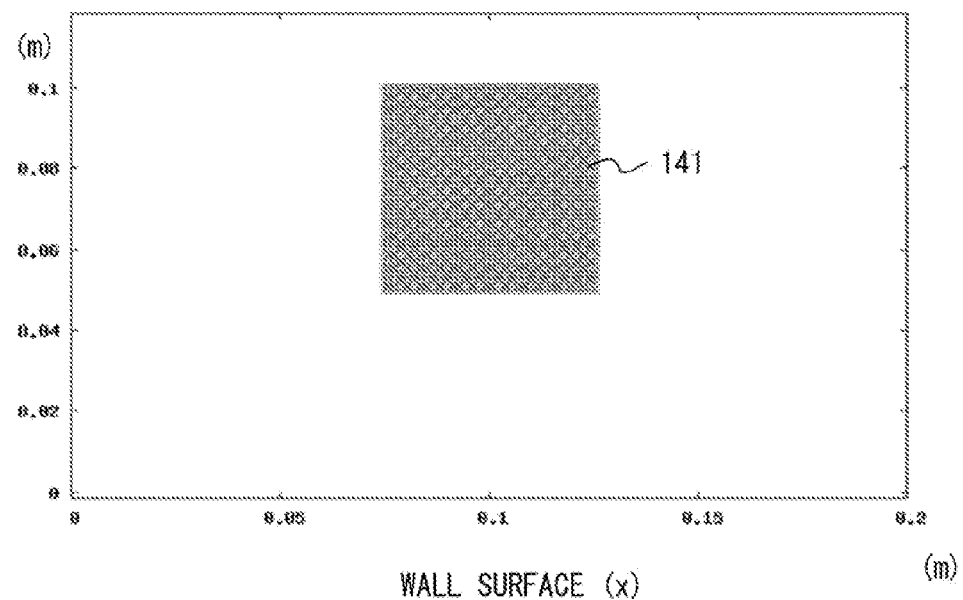
F I G. 1 4

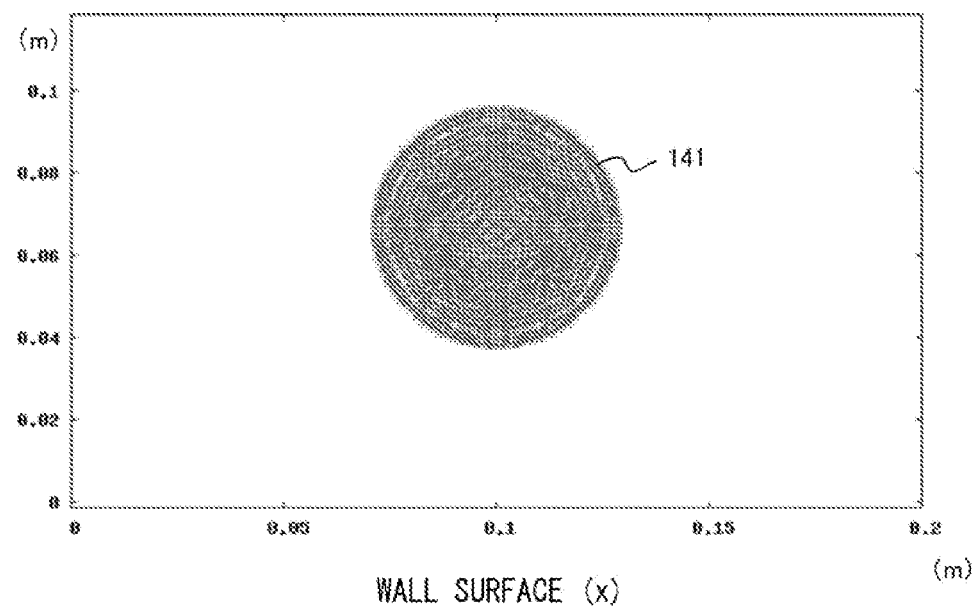
F I G. 1 5

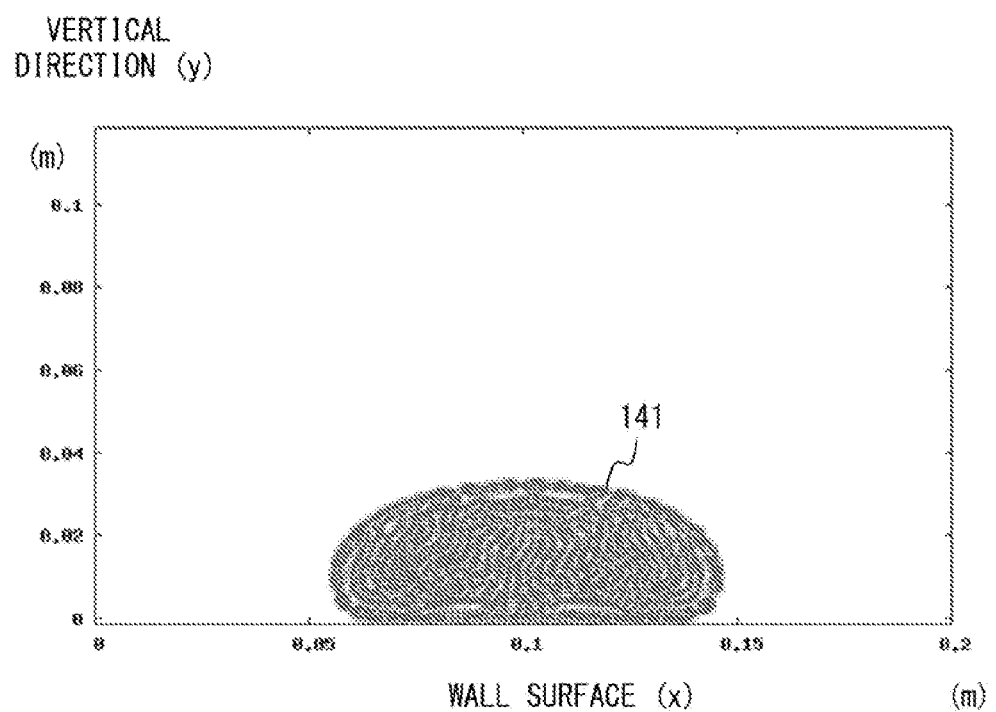
F I G. 1 7

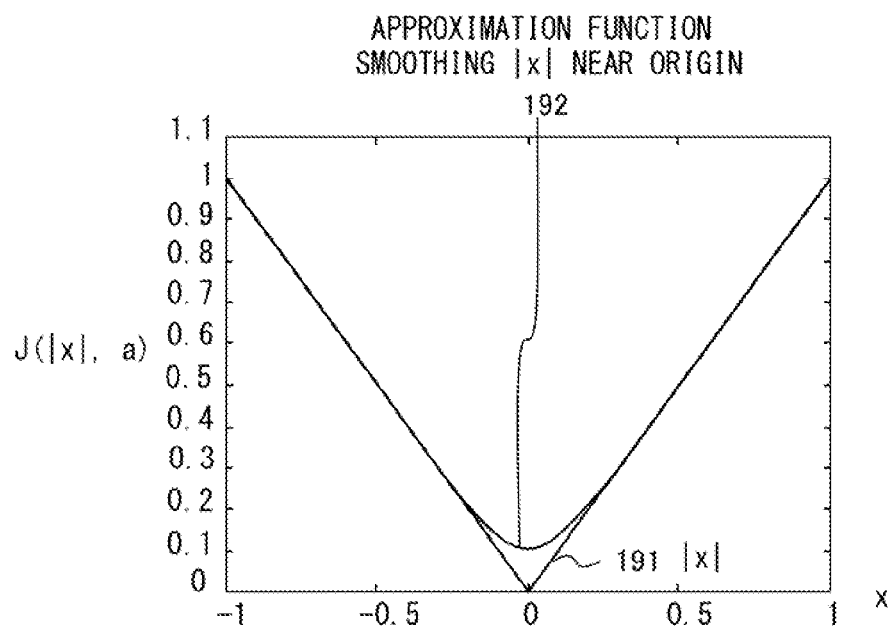
F I G. 19

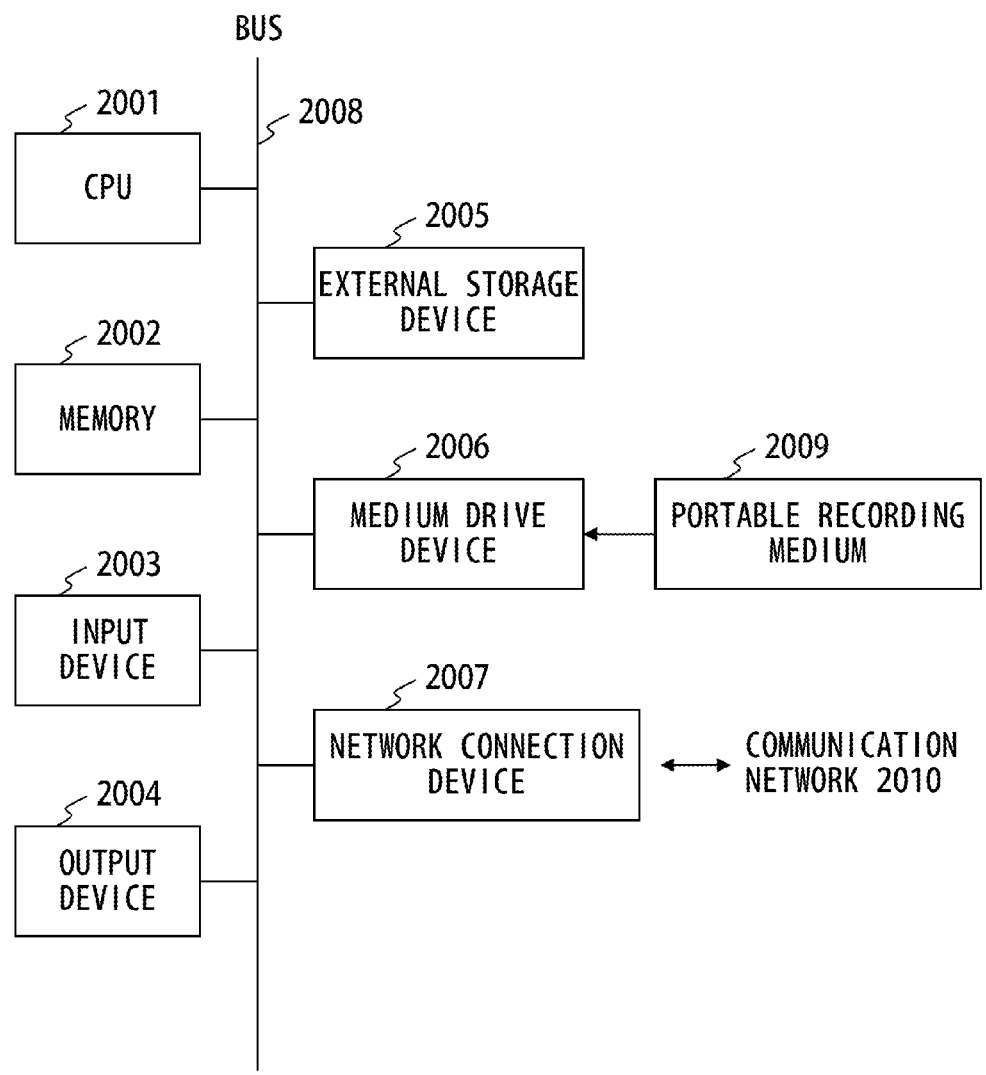
F I G. 20

COMPUTER-READABLE RECORDING MEDIUM, SIMULATION METHOD, AND SIMULATION DEVICE

CROSS-REFERENCE TO RELATED APPLICATION

This application is a continuation application of International Application PCT/JP2012/055697 filed on Mar. 6, 2012 and designated the U.S., the entire contents of which are incorporated herein by reference.

FIELD

The embodiments discussed herein are related to a computer-readable recording medium, a simulation method, and a simulation device.

BACKGROUND

As computing power of computers has improved in recent years, methods for computer simulations have developed. As a result, computer simulations have been used for various fields of application.

As numerical calculation methods for solving problems of the continuum such as in fluids and elastic bodies, the finite difference method, finite element method, or finite volume method or the like for solving the approximate solution of a differential equation on the basis of a mesh have often been used. Since numerical calculation has been utilized in fields of application such as CAE (Computer Aided Engineering), these numerical calculation methods have developed, and problems in which a fluid and a structure interact with each other have been solved.

However, in a method for using a mesh for numerical calculation, handling of cases where a moving boundary is generated is complicated, such as in a problem in which an interface such as a free surface is present and in a fluid-structure interaction problem, so program creation is often difficult.

In contrast, in a particle method (such as an MPS (Moving Particle Semi-implicit) method, SPH (Smoothed Particle Hydrodynamics) method, or the like) in which a mesh is not used for numerical calculation, special treatment is not needed in the handling of the moving boundary. Therefore, particle methods have been widely used in recent years.

FIG. 1 is a diagram explaining a problem of the particle method.

The particle method has been developed with an aim of handling easily a boundary which deforms and moves, such as a free surface or the like. Since the continuum becomes a mere particle group composed of particles 11 due to a discretization method, where the boundary surface of the continuum exists is unclear, as illustrated in FIG. 1. Therefore, there has been no unified method in the particle method for problems in which a boundary of surface tension or the like has to be visibly treated.

As for finite difference method and finite element method, there exists a calculation method for surface tension called a CSF (Continuum Surface Force) model (for example, see Non-Patent Document 1). The CSF model was applied to the particle method by X. Y. Hu, and N. A. Adams, and the calculation of surface tension by the particle method was thereby enabled (for example, see Non-Patent Document 2). In addition, there exists a method for determining surface tension as an interaction between particles (for example, see Patent Document 1), and a method for determining surface tension on the basis of deviation of neighboring particles from the position of the center of gravity (for example, see Non-Patent Documents 3, 4).

Here, an outline of the calculation method based on the CSF model applied to the particle method will be explained.

FIG. 2 is a diagram illustrating an influence radius and a continuous function obtained by overlapping kernel functions.

First, a color function $\langle C_i \rangle$ used for calculation of surface tension is defined as follows:

$$\langle C_i \rangle = \sum_j \frac{m_j}{\rho_j} W(|r_i - r_j|, h) \quad \text{[Formula 1]}$$

wherein a subscript i expresses the value of i-th particle 11, and j expresses the value of j-th particle 11.

r,m,ρ are the position vector, mass, and density of the particle 11, respectively, and a value is given to each particle 11.

W is an overlap of kernel functions 22 used in the SPH method, and a cubic spline function 23 or the like is often used.

h expresses a radius of a spherical area in which the value of the kernel function 22 is non-zero, and is called as an influence radius 21 as illustrated in FIG. 2.

The gradient of the color function ($\nabla C_i$) is a standard method for the SPH method, and is calculated as follows.

$$\nabla C_i = \rho_i \sum_j m_j \left( \frac{\langle C_j \rangle}{\rho_j^2} + \frac{\langle C_i \rangle}{\rho_i^2} \right) \frac{\partial W(|r_i - r_j|, h)}{\partial r_i} \quad \text{[Formula 2]}$$

The surface tension applied to the particle i is defined as follows using the above [Formula 2].

$$f_{s,i} = \sum_j m_i m_j \left( \frac{T_i + T_j}{\rho_i \rho_j} \right) \frac{r_i - r_j}{|r_i - r_j|} W'(|r_i - r_j|, h) \quad \text{[Formula 3]}$$

wherein $$T_i = \Gamma_g \frac{1}{|\nabla C_i|} \left( \frac{1}{d} I |\nabla C_i|^2 - \nabla C_i \otimes \nabla C_i \right).$$

$\Gamma_g$ is a surface tension coefficient, d is the dimension(s), and

I is an identity matrix.

The calculation method based on the CSF model is a calculation method for performing time development using the surface tension obtained by the above [Formula 3].

FIGS. 3-7 are diagrams illustrating the temporal changes of the result of using the conventional calculation method based on the CSF model.

As illustrated in FIGS. 3-7, in the calculation method based on the CSF model, a fluid parcel falls due to gravity receiving the influence of surface tension, and collides against a plane surface. The calculation method disclosed in Non-patent Document 2 is used for the calculation of the behaviors illustrated in FIGS. 3-7. In FIGS. 3-7, the vertical direction is set to be the y-axis so that y=0 expresses a wall surface, and the fluid 31 cannot enter the position where y<0.

As illustrated in FIG. 3, the initial shape of the fluid 31 is a square of 0.05[m]×0.05[m]. In addition,
$\Gamma_g$=10
[N/m²],
$\rho_l$=1000
[kg/m³],
h=0.0046875
[m],
c=109.8
[m/s],
dt=1.423×10⁻⁶
[s], viscosity
μ
is 0.001[m²/s], gravity acceleration
g=9.8
[m²/s], and a cubic spline function is used as a kernel function. The particles in the initial state are positioned in a uniform grid pattern (33 particles per side, for a total of 1,089 particles), and the velocity of all particles is zero.

As for the calculation results, as illustrated in FIG. 4, the distribution of the fluid 31 is in a smooth circular shape at time 0.04[s], and as illustrated in FIG. 5, the fluid 31 collides against the wall at time 0.14[s] and greatly deforms.

[Patent Document 1] Japanese Laid-open Patent Publication No. 2008-111675

[Non-Patent Document 1] B. Lafaurie, C. Nardone, R. Scardovelli, S. Zaleski, and G. Zanetti, "Modelling Merging and Fragmentation in Multiphase Flows with SuRFER", *Journal of Computational Physics,* 113, 134, 147, (1994)

[Non-Patent Document 2] X. Y. Hu, N. A. Adams, "A multiphase SPH method for macroscopic and mesoscopic flows", *Journal of Computational Physics,* 213, pp. 844-861 (2006)

[Non-Patent Document 3] T. Hongo, M. Shigeta, S. Izawa, and Y. Fukunishi, "Sanjigen Hiassuku SPH Hou ni okeru Kiekikaimen ni Sayousuru Hyoumenchouryokumoderu (Surface Tension Model Acting on Gas-Liquid Interface in Three-Dimensional Incompressible SPH Method)" *Dai 23 kai Suuchi Ryuutairikigaku shinpojiumu* (*The* 23rd *Numerical Fluid Dynamics Symposium*), A8-5 (2009)

[Non-Patent Document 4] M. Agawa, M. Shigeta, S. Izawa, and Y. Fukunishi, "Shamenjyo wo Ryuugesuru Ekitai no Hiasshuku SPH Simureshon (Incompressible SPH Simulation of Fluid Flowing Down on Slope)", *Dai 23 kai Suuchi Ryuutairikigaku shinpojiumu* (*The* 23rd *Numerical Fluid Dynamics Symposium*), A9-4 (2009)

SUMMARY

However, in the abovementioned conventional method for calculating the surface tension, there is a problem wherein a behavior generating unnatural velocity distribution in the fluid 31 sometimes appears when the collided fluid 31 greatly deforms.

In the abovementioned example, the shape is lost at time 0.7 [s] as illustrated in FIG. 6, and unnaturally distributed velocity distributions 32 are generated as illustrated in FIG. 7.

In one proposal, according to an aspect of a computer-readable recording medium having stored therein a program for causing a computer to execute a process for simulating a temporal shape change in a fluid, the process includes calculating, with respect to a fluid model based on a particle method, the model representing the fluid as a collection of particles, a surface tension of an interface against another phase by using a function to calculate a surface energy of the interface, and calculating the shape change in the fluid on the basis of the calculated surface tension.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 2 is a diagram illustrating an influence radius and a continuous function obtained by overlapping kernel functions.

FIG. 5 is a diagram illustrating the temporal change in the result of using the conventional calculation method based on the CSF model (time=0.14 [s]).

FIG. 8 is a diagram for explaining surface tension coefficients.

FIG. 12 is a diagram for explaining a state in which a particle collides against a wall surface.

FIG. 14 is a diagram illustrating the temporal change in the result of using the simulation processing to which the present invention is applied, with respect to the shape of the fluid (time=0 [s]).

FIG. 15 is a diagram illustrating the temporal change in the result of using the simulation processing to which the present invention is applied, with respect to the shape of the fluid (time=0.04 [s]).

FIG. 17 is a diagram illustrating the temporal change in the result of using the simulation processing to which the present invention is applied, with respect to the shape of the fluid (time=0.7 [s]).

FIG. 19 is a diagram illustrating the effect of an approximation function in a second embodiment.

FIG. 20 is a diagram illustrating the configuration of an information processing device.

DESCRIPTION OF EMBODIMENTS

Hereinafter, embodiments of the present invention will be described in detail referring to the diagrams.

The embodiments to which the present invention is applied are a simulation program to be executed by a computer, a simulation method, and a simulation device. A fluid as a target of simulation is recognized as a collection of particles, surface tension, which is an interaction force between particles on the basis of variation, is calculated using a predetermined approximation function, and the shape change in the fluid is simulated by using the calculated surface tension.

First Embodiment

FIG. 8 is a diagram for explaining surface tension coefficients.

In general, the surface energy of a fluid can be defined as follows:

$$E_s = \oint \Gamma_g \chi dS + \oint \Gamma_s (1-\chi) dS. \quad \text{[Formula 4]}$$

The above surface energy is calculated by discretizing it by a particle method, and the surface tension applied to fluid particles can be determined by a first variation.

Here, the domain of integration of the right side of the above [Formula 4] is the whole area of the boundary surface of the fluid, and $\chi$ is 1 in a portion where the fluid is in contact with the air, and is zero in a portion other than this portion.

$\Gamma_g, \Gamma_s$ are the surface tension coefficient of the portion in contact with the air, and the surface tension coefficient of a portion in contact with a solid, respectively, as illustrated in FIG. 8.

Figure 9:
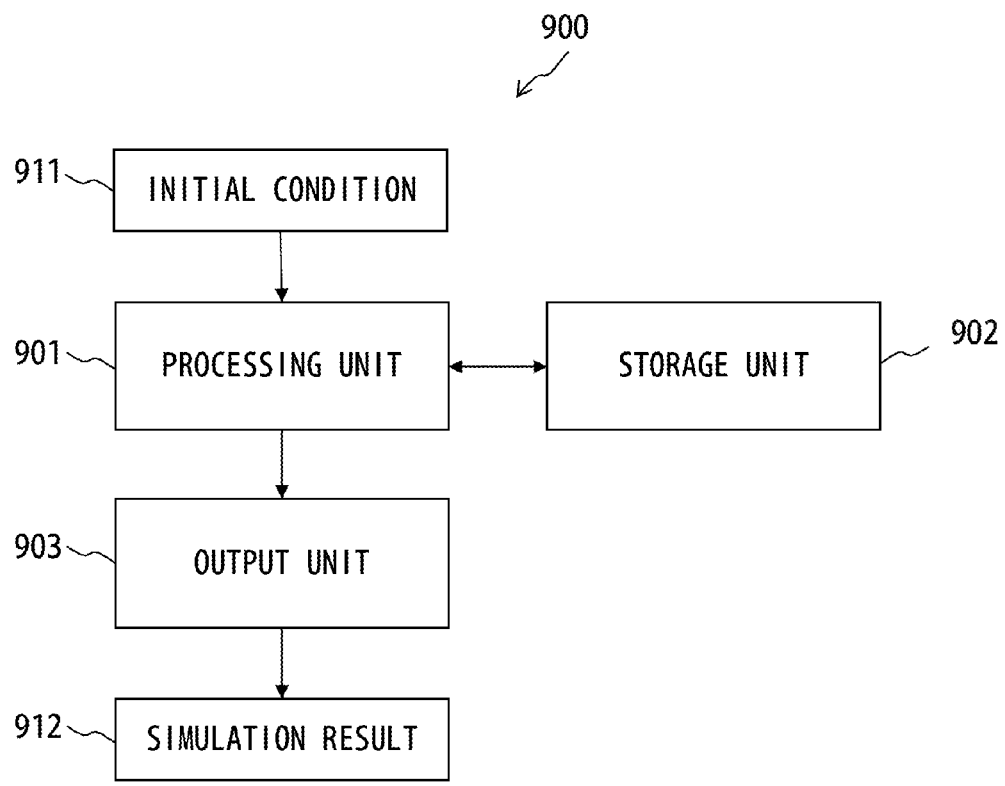
FIG. 9 is a diagram illustrating a configuration example of a simulation device to which the present invention is applied.

FIG. 9 is a diagram illustrating a configuration example of a simulation device to which the present invention is applied.

In FIG. 9, the simulation device 900 includes a processing unit 901, a storage unit 902, and an output unit 903. The simulation device 900 performs numerical calculation on the basis of the particle method expressing the continuum of a fluid or the like as a collection of particles using an approximation function described hereinafter, to calculate the surface tension. The shape change in the continuum is calculated using the calculation result, and the simulation result 912 is output.

The storage unit 902 stores information of each calculation formula used when executing the simulation program to which the present invention is applied.

The processing unit 901 executes simulation processing to which the present invention is applied, the simulation processing being described hereinafter as the first and second embodiments.

The output unit 903 outputs the simulation result 912 executed by the processing unit 901.

First, a method for calculating the surface tension using the approximation function will be described.

Integration of the above [Formula 4] is defined as the approximation function of the following [Formula 5].

$$E_{s,p1}(r_1, r_2, \ldots, r_n) = \sum_i Q\left(\frac{m_i}{\rho_i}\right)^{1-\frac{1}{d}}((\Gamma_g - \Gamma_s)\chi(l_i, \varepsilon) + \Gamma_s)\langle s\rangle_i$$

wherein,

Q is a constant and is determined so as to match the oscillating period of a surface-tension wave.

d is the dimension(s) of a space, $\Gamma_g, \Gamma_s$ are surface tension when the liquid is in contact with the air, and surface tension when the liquid is in contact with a solid, respectively.

$f_i$ is a function determined on the basis of the position of a particle, and $$\langle s\rangle_i = \sum_j \frac{m_j}{\rho_j} f(1-s_j, 1-s_{min,j}) W(|r_i - r_j|, h)$$

$$s_i = \sum_j \frac{m_j}{\rho_j} W(|r_i - r_j|, h), \quad s_{min,i} = \frac{m_i}{\rho_i} W(0, h)$$

$$f(x, h) = \begin{cases} 1 & \frac{x}{h} \geq 1 \\ 3\left(\frac{x}{h}\right)^2 - 2\left(\frac{x}{h}\right)^3 & 0 \leq \frac{x}{h} < 1 \\ 0 & \frac{x}{h} < 0 \end{cases}$$

Figure 10:
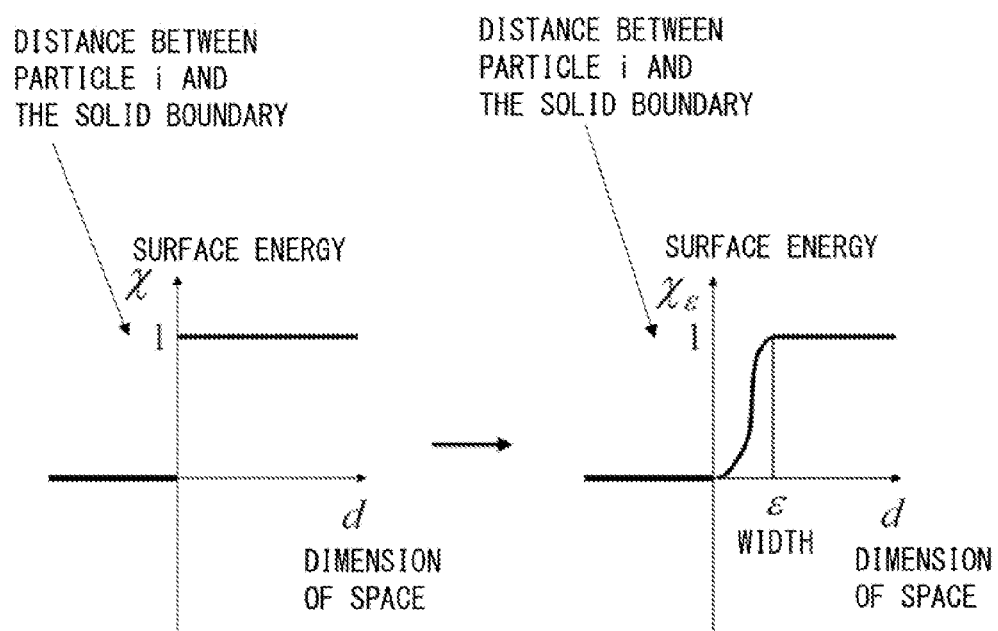
FIG. 10 is a diagram for explaining a function smoothly approximating surface energy χ with width ϵ.

FIG. 10 is a diagram for explaining the function smoothly approximating surface energy $\chi$ with width $\varepsilon$.

In Formula 5, $\chi(l, \varepsilon)$ is a function smoothly approximating $\chi$ in Formula 4 with the width $\varepsilon$ as illustrated in FIG. 10, and $l_i$ is a distance between the particle i and the solid boundary.

$$\left(\frac{m_j}{\rho_j}\right)^{1-\frac{1}{d}}$$

has the dimension(s) of the area, and in the SPH method, $S_i$ becomes close to 1 in the particle inside the fluid, becomes smaller near the surface, and if there are no particles within an influence radius h, becomes $S_{min,i}$.

The approximation function defined as [Formula 5] sums the quantity having the same dimension(s) as the length of the particle on the fluid surface, and is considered to be approximating the surface integration of [Formula 4].

The gradient of the surface energy discretized by the particle method is calculated in [Formula 5], and the net surface tension acting on each particle is derived as follows:

$$f_{k,s1} = -\frac{\partial}{\partial r_k} E_{s,p1}(r_1, r_2, \ldots, r_n) \approx \quad \text{[Formula 6]}$$

$$Q \sum_j \left[ (\Gamma_g - \Gamma_s) \left( \frac{m_k}{\rho_k} \left( \frac{m_j}{\rho_j} \right)^{1-\frac{1}{d}} f_k \chi_j + \frac{m_j}{\rho_j} \left( \frac{m_k}{\rho_k} \right)^{1-\frac{1}{d}} f_j \chi_k \right) + \right.$$

$$\left. \Gamma_s \left( \frac{m_k}{\rho_k} \left( \frac{m_j}{\rho_j} \right)^{1-\frac{1}{d}} f_k + \frac{m_j}{\rho_j} \left( \frac{m_k}{\rho_k} \right)^{1-\frac{1}{d}} f_j \right) \right]$$

$$\frac{\partial W(|r_k - r_j|, h)}{\partial r_k} -$$

$$Q(\Gamma_g - \Gamma_s) \sum_j \frac{m_j}{\rho_j} \left( \frac{m_k}{\rho_k} \right)^{1-\frac{1}{d}} f_j \frac{\partial \chi_k}{\partial r_k} W(|r_k - r_j|)$$

The calculation of the surface tension using the approximation function was described hereinbefore.

Next, calculation of the shape change in the fluid will be described using the surface tension calculated in the above-mentioned manner.

Figure 11:
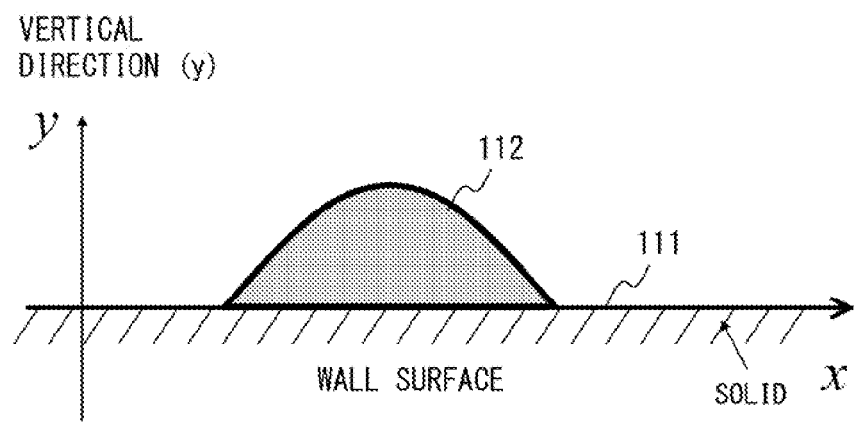
FIG. 11 a diagram illustrating an example of a two-dimensional fluid.

FIG. 11 is a diagram illustrating an example of a two-dimensional fluid, with the y-axis set in the vertical direction from a plain surface which is a wall surface, and the x-axis set along the wall surface.

An equation of motion of an incompressible viscous fluid in a fluid 112 placed on the plane surface of a solid 111 in a situation like FIG. 11, that is, y=0, will be discussed.

In $$\frac{D\rho}{Dt} = -\rho \nabla \cdot v, \quad \text{[Formula 7]}$$

$$\rho \frac{Dv}{Dt} = -\nabla p + \nabla \cdot \Pi - g\hat{y}, \quad \text{[Formula 8]}$$

$$p = c^2(\rho - \rho_0), \quad \text{[Formula 9]}$$

[Formula 7], [Formula 8], and [Formula 9] are the law of conservation of mass, the law of conservation of momentum, and a state equation, respectively.

$$\rho(r,t), v(r,t), p(r,t), c \quad \text{[Formula 10]}$$

are the density field, velocity field, pressure field, and sonic velocity of the fluid 112, respectively.
Π
is a viscous stress tensor, and if the viscous coefficient of the fluid 112 is set as
μ
(a constant), $$\Pi = \frac{\mu}{2}(\nabla v + \nabla v^T).$$

[Formula 7] expresses the effect of increasing a density in a velocity field in which the fluid 112 gathers, and expresses in contrast the effect of decreasing a density in a velocity field in which the fluid 112 separates. A first term on the right side of [Formula 8] is a pressure gradient term and expresses the effect that force is generated from a portion in which pressure is strong toward a portion in which pressure is weak in the fluid 112. A second term on the right side is a viscous stress term and expresses the effect of slowing down the flow of the fluid. A third term on the right side is a gravity term.

g
is gravity acceleration,
y
is a unit vector in the y direction.

In the first embodiment, the relation of only density and pressure such as in [Formula 9] is used. However, a general state equation using temperature, internal energy, entropy, and the like may be used.

In addition, to the portion in contact with the air, a surface tension coefficient (constant) of
$\Gamma_g$
is considered to be applied, and to the portion in contact with the solid 111, a surface tension coefficient (constant) of
$\Gamma_s$
is considered to be applied.

Then, [Formulas 7-9] are discretized as follows using the SPH method, and the abovementioned surface tension terms are introduced.

$$r_i^* = r_i^n + \frac{dt}{2} v_i^n,$$

Here, an x component and y component of
$r_i^*$
calculated in [Formula 10] are set as
$x_i^*$,
$y_i^*$
respectively, and the component of an i-th velocity is set as
$v_{i,x}^n, v_{i,y}^n$
to perform the following calculation.

$$\bar{r}_i^* = \begin{cases} r_i^n & y_i^* > 0 \\ r_i^n - \frac{y_i^*}{v_{i,y}^n} v_i^n & y_i^* \leq 0 \end{cases}, \quad \text{[Formula 11]}$$

$$\bar{v}_i^n = \begin{cases} v_i^n & y_i^* > 0 \\ \left(1 - \frac{y_i^*}{dt v_{i,y}^n}\right) v_i^n & y_i^* \leq 0 \end{cases}$$

$$v_i^{*,n+1} = \bar{v}_i^n - \quad \text{[Formula 12]}$$

$$2dt \left[ \sum_j m_j \left( \frac{p_{ij}^{n+1/2}}{\rho_i \rho_j} \right) \left( \frac{L(\bar{r}_i^*) + L(\bar{r}_j^*)}{2} \right) \frac{\partial W(|\bar{r}_i^* - \bar{r}_j^*|, h)}{\partial \bar{r}_i^*} \right] -$$

$$\frac{1}{2} \sum_j m_j \left( \frac{4\mu \xi}{\rho_i \rho_j} \frac{(\bar{v}_i^n - \bar{v}_j^n) \cdot (\bar{r}_i^* - \bar{r}_j^*)}{|\bar{r}_i^* - \bar{r}_j^*|^2 + \eta^2} \right) v_{ij}^j \frac{\partial W(|\bar{r}_i^* - \bar{r}_j^*|, h)}{\partial \bar{r}_i^*} -$$

$$g\hat{y} + \frac{f_{ij}}{m_i} + \frac{f_{i,s1}}{m_i},$$

$$r_i^{*,n+1} = \bar{r}_i^* + \frac{dt}{2} v_i^{*,n+1} \quad \text{[Formula 13]}$$

$$r_i^{n+1} = \begin{cases} r_i^{*,n+1} & y_i^{*,n+1} > 0 \\ r_i^{*,n+1} - \frac{y_i^{*,n+1}}{v_{i,y}^{*,n+1}} v_i^{*,n+1} & y_i^{*,n+1} \leq 0 \end{cases}, \quad \text{[Formula 14]}$$

$$v_i^{n+1} = \begin{cases} v_i^{*,n+1} & y_i^{*,n+1} > 0 \\ \left(1 - \frac{y_i^{*,n+1}}{dt v_{i,y}^{*,n+1}}\right) v_i^{*,n+1} & y_i^{*,n+1} \leq 0 \end{cases}$$

-continued $$\rho_i^{n+1} = \rho_i^n + 2dt \sum_j \frac{m_j \rho_i^n}{\rho_j^n} \left( \frac{v_i^{s,n+1} + \overline{v}_i^{s,n}}{2} - v_{ij}^{s,n+1/2} \right) \frac{\partial}{\partial (|\vec{r}_i^* - \vec{r}_j^*|)} W(|\vec{r}_i^* - \vec{r}_j^*|, h),$$ [Formula 15]

wherein a subscript expresses the number of the particle; that is, the position vector, velocity vector, density, and pressure of the i-th particle are $r_i$, $v_i$, $\rho_i$, $p_i$ respectively.

$m_j$ is the mass of the j-th particle.

$\xi, \eta$ are constants introduced to calculate a viscous term.

[Formula 12] discretizes the equation of motion of [Formula 8] by the particle method, a second term on the right side expresses a pressure gradient term, and a third term on the right side expresses a viscous stress term. A fifth term on the right side of [Formula 12] is a force for preventing the distance between particles from becoming too close, and if $r_{min}$ is a constant, $$f_{ij} = \frac{8}{r_{min}^2} \left( 1 - \left( \frac{|\vec{r}_i^* - \vec{r}_j^*|}{r_{min}} \right)^2 \right)^3 \frac{\vec{r}_i^* - \vec{r}_j^*}{|\vec{r}_i^* - \vec{r}_j^*|}$$

A sixth term on the right side, $f_{i,s1}$ is a force generated by the abovementioned surface tension and [Formula 6] is applied thereto; however in the abovementioned simulation case, since the plain surface of y=0 is the wall surface of the solid 111, $\chi_i = \chi_i(\overline{y}_i^*, \epsilon)$ FIG. 12 is a diagram for explaining the state in which the particle collides against the wall surface.

The abovementioned [Formula 12] and [Formula 14] express a practical correction in which the particle stops at the moment when it collides against the wall surface as illustrated in the lower part of FIG. 12 instead of going through the wall surface as it is as illustrated in the upper part of FIG. 12 when the position of the particle is moved and the particle is going through the wall surface positioned on the plain surface of y=0.

Here, $L(\vec{r}_i^*)$ is a renormalization matrix of $$L(r_i) = \left[ \sum_j \frac{m_j}{\rho_j} (r_j - r_i) \otimes \frac{\partial}{\partial r_i} W(|r_i - r_j|, h) \right]^{-1}.$$

And in addition, $$\vec{n}_{ij}^* = \left( \frac{L(\vec{r}_j^*) + L(\vec{r}_i^*)}{2} \right) \frac{\vec{r}_i^* - \vec{r}_j^*}{|\vec{r}_i^* - \vec{r}_j^*|}.$$

$v_i^{s,n} = \overline{v}_i^n \cdot \vec{n}_{ij}^*,$ $v_j^{s,n} = \overline{v}_j^n \cdot \vec{n}_{ij}^*$ -continued $p_{ij}^{n+1/2}$, $v_{ij}^{s,n+1/2}$ are intermediate values of space-time determined by solving the one-dimensional Riemann problem between the particles i and j. Specifically, the values are determined as follows.

First, the following characteristic quantities are set with respect to the particles i and j.

$$q_i^{n,+} = \log(\rho_i^n) + \frac{v_i^{s,n}}{c}$$ [Formula 16]

$$q_i^{n,-} = \log(\rho_i^n) - \frac{v_i^{s,n}}{c}$$ [Formula 17]

$$q_j^{n,+} = \log(\rho_j^n) + \frac{v_j^{s,n}}{c}$$ [Formula 18]

$$q_j^{n,-} = \log(\rho_j^n) - \frac{v_j^{s,n}}{c}$$ [Formula 19]

In addition, each gradient is calculated as follows:

$$\nabla \log(\rho)|_i = \sum_k \frac{m_k}{\rho_i} (\log(\rho_k^n) - \log(\rho_i^n)) L(\vec{r}_i^*) \frac{\partial W(|\vec{r}_i^* - \vec{r}_k^*|, h)}{\partial \vec{r}_i^*}$$ [Formula 20]

$$\nabla v|_i = \sum_k \frac{m_k}{\rho_i} L(\vec{r}_i^*) \frac{\partial W(|\vec{r}_i^* - \vec{r}_k^*|, h)}{\partial \vec{r}_i^*} \otimes (\vec{v}_k^n - \vec{v}_i^n)$$ [Formula 21]

$$\nabla q|_i^{n,+} = \nabla \log(\rho)|_i + \frac{\nabla v|_i \vec{n}_{ij}^*}{c}$$ [Formula 22]

$$\nabla q|_j^{n,+} = \nabla \log(\rho)|_j + \frac{\nabla v|_j \vec{n}_{ij}^*}{c}$$ [Formula 23]

$$\nabla q|_i^{n,-} = \nabla \log(\rho)|_i - \frac{\nabla v|_i \vec{n}_{ij}^*}{c}$$ [Formula 24]

$$\nabla q|_j^{n,-} = \nabla \log(\rho)|_j - \frac{\nabla v|_j \vec{n}_{ij}^*}{c}$$ [Formula 25]

wherein, $\vec{r}_{ij}^* = \vec{r}_i^* - \vec{r}_j^*$ $r_{ij}^* = |\vec{r}_{ij}^*|$ and using the above quantities, $p_{ij}^{n+1/2}$, $v_{ij}^{s,n+1/2}$ are determined as follows:

$$q_{ij}^{n+1/2,+} = q_j^{n,+} + \left( \frac{|\vec{r}_{ij}^*|}{2} - \frac{cdt}{2} \right)(\vec{r}_{ij}^* \cdot \nabla q|_j^{n,+})$$ [Formula 26]

$$q_{ij}^{n+1/2,-} = q_i^{n,+} - \left( \frac{|\vec{r}_{ij}^*|}{2} + \frac{cdt}{2} \right)(\vec{r}_{ij}^* \cdot \nabla q|_i^{n,-})$$ [Formula 27]

$$\rho_{ij}^{n+1/2} = \exp\left( \frac{q_{ij}^{n+1/2,+} + q_{ij}^{n+1/2,-}}{2} \right)$$ [Formula 28]

$$v_{ij}^{n+1/2} = c\left( \frac{q_{ij}^{n+1/2,+} - q_{ij}^{n+1/2,-}}{2} \right)$$ [Formula 29]

$$p_{ij}^{n+1/2} = c^2(\rho_{ij}^{n+1/2} + \rho_0).$$ [Formula 30]

Figure 13:
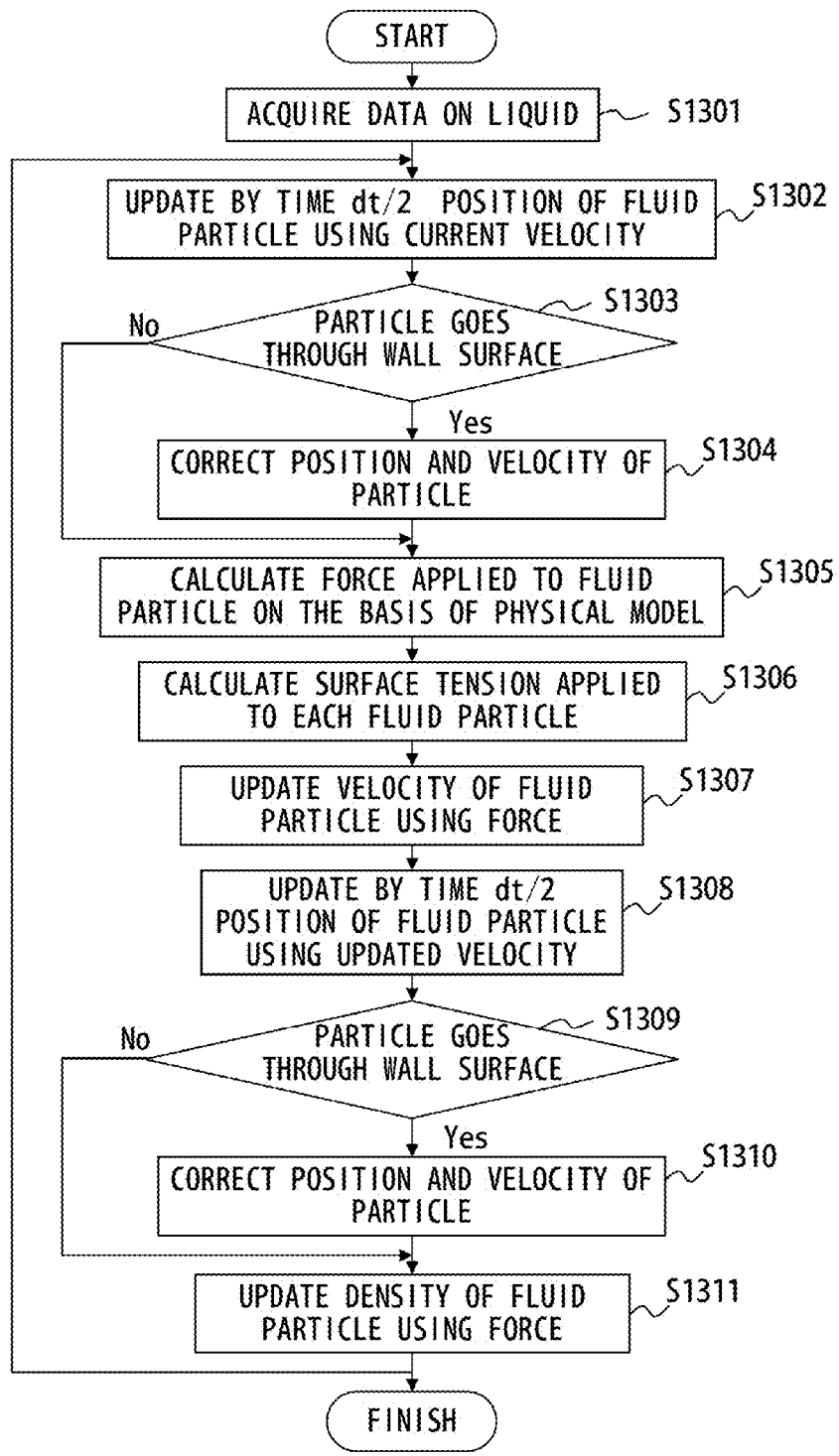
FIG. 13 is a flowchart illustrating the flow of simulation processing to which the present invention is applied.

FIG. 13 is a flowchart illustrating the flow of simulation processing to which the present invention is applied.

First, in step S1301, the position vector and velocity vector of each particle is obtained as data of the physical quantity of the fluid of a simulation target. In step S1302, by using the abovementioned [Formula 9] the position of the particle is updated to the position after time dt/2 passes using the current velocity.

Then, in classification of cases on the basis of the value of y in [Formula 11], if the result is y<0, that is, if it is determined that the particle goes through the wall surface (step S1303: Yes), in step S1304, the position and velocity of the particle is corrected so that the particle does not go through the wall surface, that is, y≥0, using the abovementioned [Formula 11].

On the other hand, in classification of cases on the basis of the value of y in [Formula 11], if the result is y≥0, that is, if it is determined that the particle does not go through the wall surface (step S1303: No), the position and velocity of the particle are not corrected.

Next, in step S1305, a force applied to the fluid particle is calculated on the basis of a physics model by calculating the second to fifth terms on the right side of the abovementioned [Formula 12].

In step S1306, the surface tension related to each fluid particle is calculated by calculating the sixth term on the right side of the abovementioned [Formula 12].

When the calculation of the surface tension on each boundary particle is finished, the velocity of the fluid particle is updated in step S1307.

Next, in step 1308, the position of the fluid particle is updated to the position after time dt/2 passes using the velocity updated in step S1307, using the abovementioned [Formula 13].

Then, in classification of cases on the basis of the value of y in [Formula 14], if the result is y<0, that is, if it is determined that the particle goes through the wall surface (step S1309: Yes), in step 1310, the position and velocity of the particle is corrected so that the particle does not go through the wall surface, that is, y≥0, using the abovementioned [Formula 14].

On the other hand, in classification of cases on the basis of the value of y in [Formula 14], if the result is y≥0, that is, if it is determined that the particle does not go through the wall surface (step S1303: No), the position and velocity of the particle are not corrected.

Thereafter, in step S1311, the velocity of the fluid particle is updated, and the above steps S1302 to S1311 are repeatedly executed.

If the simulation processing hereinbefore described is executed, the shape of the fluid becomes as illustrated in FIGS. 14-18.

FIGS. 14-18 are diagrams illustrating the temporal change in the result of using the simulation processing to which the present invention is applied, with respect to the shape of the fluid. The calculation conditions are the same as those in the calculation by the conventional technique in FIGS. 3-7.

As illustrated in FIG. 14, the initial shape of a fluid 141 is a square of 0.05 [m]×0.05 [m]. The respective initial conditions are set as:
$\Gamma_g = \Gamma_s = 10$
[N/m$^2$],
$\rho_0 = 1000$
[kg/m$^3$],
h=0.0046875
[m],
c=109.8
[m/s],
dt=1.423×10$^{-6}$
[s],
Q=4,
viscosity
μ is 0.001 [m$^2$/S], gravity acceleration
g=9.8
[m/s$^2$],
ξ=4.9633
$r_{min}$=0.00104
[m].

The particles in the initial state are positioned in a uniform grid pattern (33 particles per side, for a total of 1,089 particles), and the velocity of all particles is zero and the density is 1,000 [kg/m$^3$].

Figure 1:
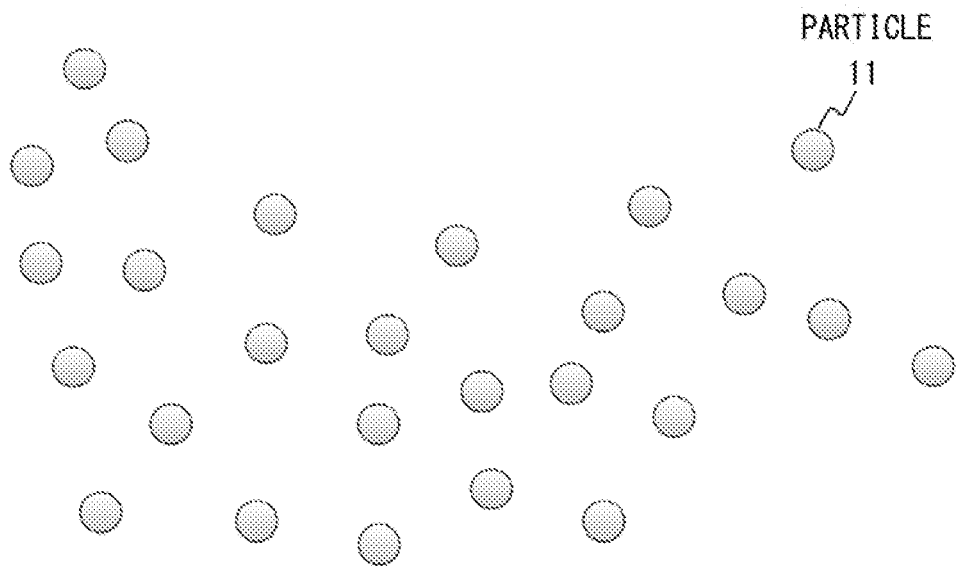
FIG. 1 is a diagram for expressing a problem of a particle method.
Figure 3:
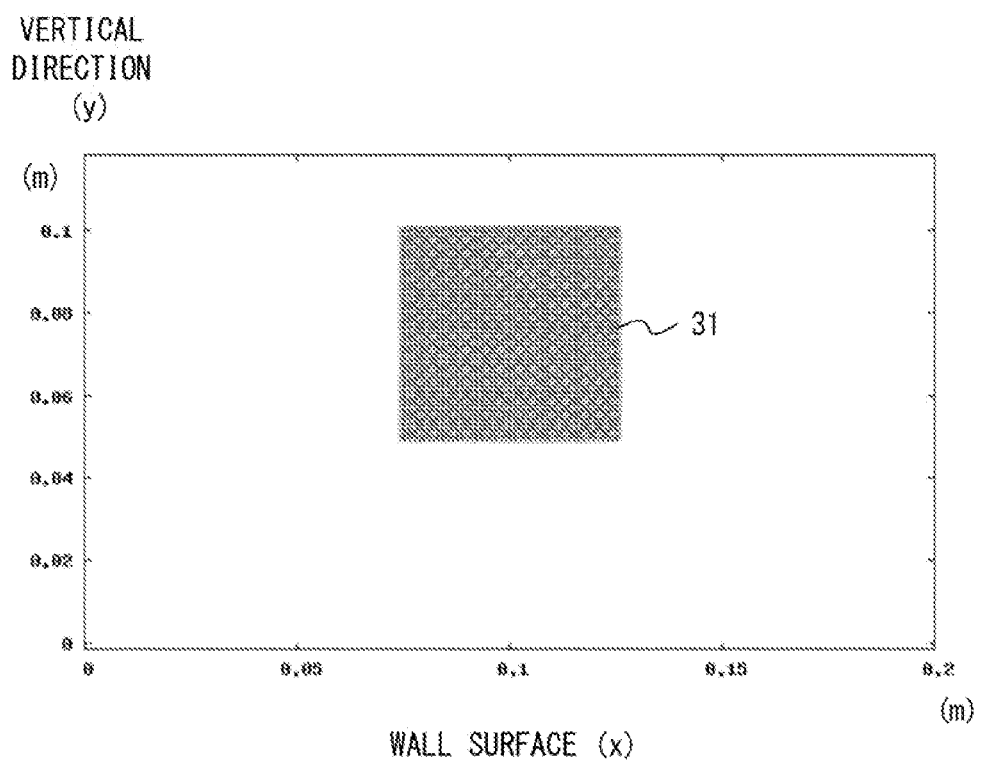
FIG. 3 is a diagram illustrating the temporal change in the result of using a conventional calculation method based on a CSF model (time=0 [s]).
Figure 4:
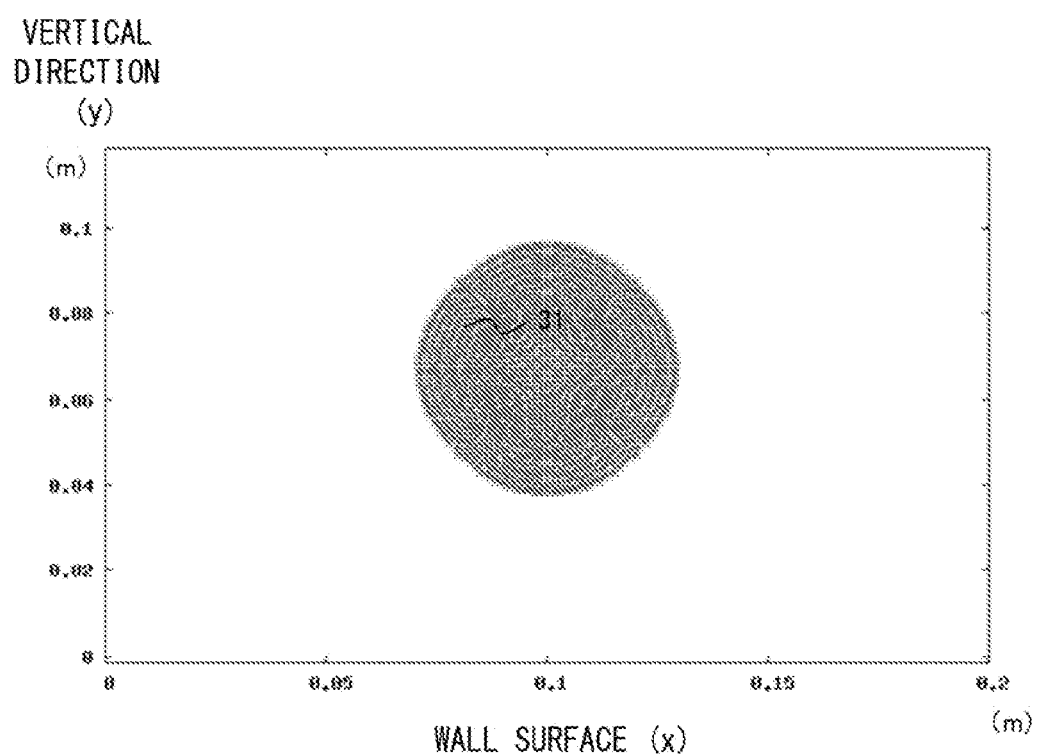
FIG. 4 is a diagram illustrating the temporal change in the result of using the conventional calculation method based on the CSF model (time=0.04 [s]).
Figure 16:
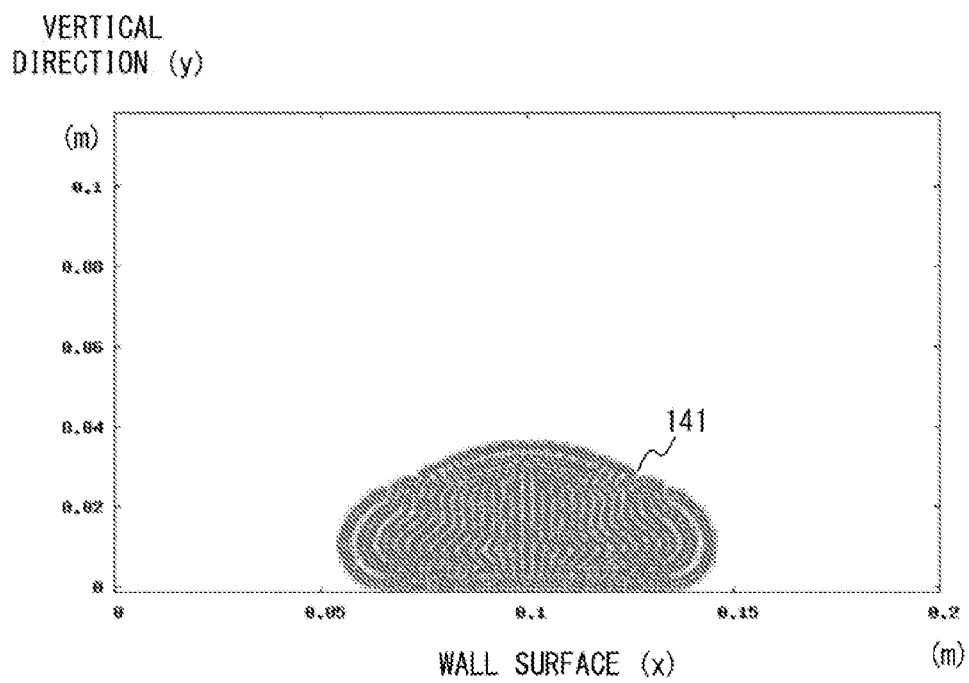
FIG. 16 is a diagram illustrating the temporal change in the result of using the simulation processing to which the present invention is applied, with respect to the shape of the fluid (time=0.14 [s]).

As for the calculation results, the distribution of the fluid 141 is in a smooth circular shape as in FIG. 4 at time 0.04 [s], and as illustrated in FIG. 16, the fluid 141 collides against the wall at time 0.14 [s] and greatly deforms.

Figure 6:
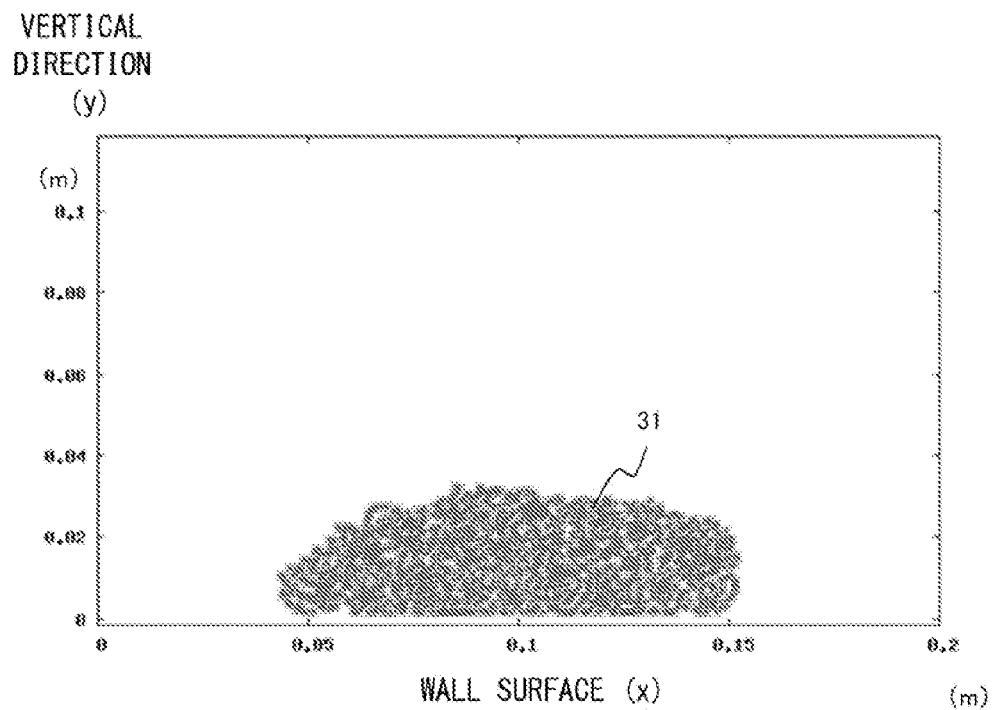
FIG. 6 is a diagram illustrating the temporal change in the result of using the conventional calculation method based on the CSF model (time=0.7 [s]).
Figure 7:
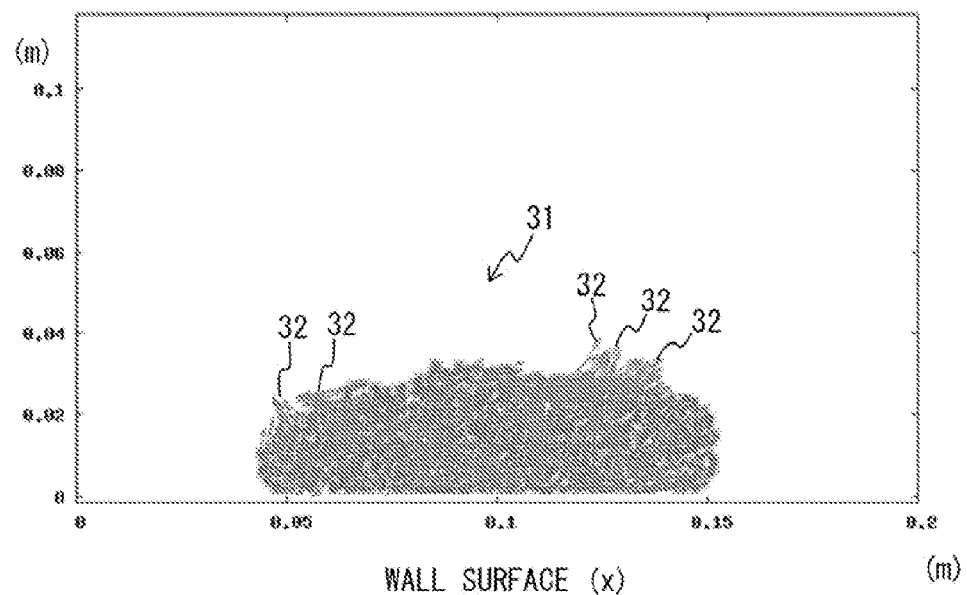
FIG. 7 is a diagram illustrating the temporal change in the result of using the conventional calculation method based on the CSF model (time=0.7 [s]: unnatural velocity distribution is generated).
Figure 18:
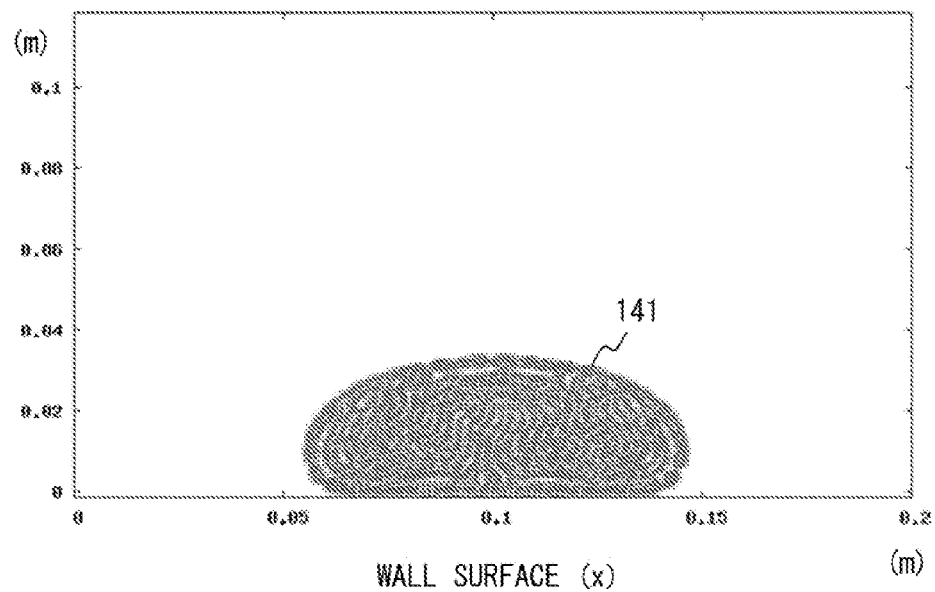
FIG. 18 is a diagram illustrating the temporal change in the result of using the simulation processing to which the present invention is applied, with respect to the shape of the fluid (time=0.7 [s]: unnatural velocity distribution is not generated).

As illustrated in FIG. 17, the shape of the fluid 141 is not lost at time 0.7[s], in contrast to the calculation result of the conventional technique illustrated in FIG. 6, and the velocity distribution is stable and the steady state is maintained as illustrated in FIG. 18.

Second Embodiment

In the second embodiment to which the present invention is applied, instead of approximating the integration of [Formula 4] like the approximation function of [Formula 5] in the abovementioned first embodiment, the integration of [Formula 4] is approximated like the approximation function of the following [Formula 31]. By replacing the pressure "p1" in the first embodiment with "p2", the description in the first embodiment can be applied to the second embodiment.

$$E_{s,p2}(r_1, r_2, \ldots, r_n) = \sum_i \frac{m_i}{\rho_i}((\Gamma_g - \Gamma_s)\chi_\varepsilon + \Gamma_s)J(|\langle \nabla C_i \rangle|, a) \quad \text{[Formula 31]}$$

wherein $$\langle \nabla C \rangle_i = \sum_j \frac{m_j}{\rho_j} L(r_i) \frac{\partial W(|r_i - r_j|, h)}{\partial r_i} \quad \text{[Formula 32]}$$

$$L(r_i) = \left[\sum_j \frac{m_j}{\rho_j} L\left(r_j - r_i \otimes \frac{\partial}{\partial r_i} W(|r_i - r_j|, h)\right)\right]^{-1} \quad \text{[Formula 33]}$$

$$J(|\langle \nabla C_i \rangle|, a)\Big| |\langle \nabla C_i \rangle| - a\left(\exp\left(\frac{-1}{a}\right) - \exp\left(\frac{|\langle \nabla C_i \rangle|}{a}\right)\right)\Big| \quad \text{[Formula 34]}$$

$\langle \nabla C \rangle_{i,i}$
has the same dimension(s) as that of the area, so it is considered that [Formula 6] approximates the surface energy.
$L_i$
is a re-standardization matrix, and corrects gradient calculation in the non-uniform distribution of the particles.

FIG. 19 is a diagram illustrating the effect of the approximation function in the second embodiment.

In the above [Formula 31],
J(|x|, a)
192 is an approximation function smoothing
|x|
191 near the origin, and
the minimum is almost the same as
a
that is, "0.1".

The net force applied to the particle k is derived as follows on the basis of the energy of [Formula 6].

$$f_{k,s2} = \begin{pmatrix} \frac{E_{s,p2}(r_1, r_2, \ldots, r_k + \delta\hat{x}, \ldots, r_n) - E_{s,p2}(r_1, r_2, \ldots, r_k - \delta\hat{x}, \ldots, r_n)}{2\delta} \\ \frac{E_{s,p2}(r_1, r_2, \ldots, r_k + \delta\hat{y}, \ldots, r_n) - E_{s,p2}(r_1, r_2, \ldots, r_k - \delta\hat{y}, \ldots, r_n)}{2\delta} \\ \frac{E_{s,p2}(r_1, r_2, \ldots, r_k + \delta\hat{z}, \ldots, r_n) - E_{s,p2}(r_1, r_2, \ldots, r_k - \delta\hat{z}, \ldots, r_n)}{2\delta} \end{pmatrix}$$ [Formula 35]

$\hat{x}, \hat{y}, \hat{z}$
are unit vectors of x, y, z directions, respectively.

As mentioned above, the present invention can be applied to the calculation of the particle method and of fluid motion in which surface tension is effective. In particular, it is effective for simulation of casting molten metal, simulation of casting resin, or the like. In addition, there is no need to configure settings to place particles on a wall surface or the like in a conventional technique, when simulating the shape change in the fluid which collides against a solid such as the wall surface or the like.

The simulation device in FIG. 9 can be materialized by using an information processing device (computer) illustrated in FIG. 20. The information processing device in FIG. 20 includes a CPU (Central Processing Unit) 2001, a memory 2002, an input device 2003, an output device 2004, an external storage device 2005, a medium drive device 2006, and a network connection device 2007. These are connected with each other through a bus 2008.

The memory 2002 is a storage device such as a ROM (Read Only Memory), RAM (Random Access Memory), flash memory or the like, and stores a program and data used for simulation processing. For example, the CPU 2001 executes the abovementioned simulation processing by executing the program using the memory 2002. The memory 2002 can also be used as the storage unit 902 in FIG. 9.

The input device 2003 is, for example, a keyboard, or a pointing device or the like, and is used for inputting an instruction from an operator or information. The output device 2004 is, for example, a display device, printer, speaker or the like, and is used for an inquiry to the operator or for output of the processing result. The output device 2004 can also be used as the output unit 903 in FIG. 9.

The external storage device 2005 is, for example, a magnetic disk device, an optical disk device, a magneto optical disk device, a tape device, or the like. A hard disk drive is included in this external storage device 2005. The information processing device stores the program and data in the external storage device 2005, and can use them by loading them into the memory 2002.

The medium drive device 2006 drives a portable recording medium 2009 to access its recorded content. The portable recording medium 2009 is a memory device, flexible disk, optical disk, magneto optical disk, or the like. A Computer Disk Read Only Memory (CD-ROM), Digital Versatile Disk (DVD), Universal Serial Bus (USB) memory and the like are included in the portable recording medium 2009. The operator can use the program and data by loading them into the memory 2002, by storing the program and data in the portable recording medium 2009.

Thus, physical (non-transitory) recording media such as the memory 2002, the external storage device 2005, and the portable recording medium 2009 are included in computer readable recording media configured to store the program and data used in the simulation processing.

The network connection device 2007 is connected to a communication network 2010, and is a communication interface executing data conversion accompanying communication. The information processing device receives the program and data from the external device via the network connection device 2007, and can use them by loading them into the memory 2002. The network connection device 2007 can also be used as the output unit 903 in FIG. 9.

The disclosed embodiments and their advantages have been described in detail; however, those skilled in the art will recognize that various modifications, additions, and omissions can be made without departing from the scope of the present invention explicitly described in the following claims.

For example, instead of the approximation function defined as [Formula 5] or [Formula 31], an appropriate approximation function can be used.

The present invention is not limited to the embodiments described above, and a wide variety of configurations or shapes can be taken within the scope not departing from the gist of the present invention.

The disclosed simulation program, simulation method, and simulation device have an effect of outputting an appropriate simulation result without expressing behaviors such as generating an unnatural velocity distribution, with respect to a fluid which is a simulation target.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable recording medium having stored therein a simulation program for causing a computer to execute a process for suppressing behaviors including generating an unnatural velocity distribution when simulating a temporal shape change in a fluid, the process comprising:

obtaining a position vector and a velocity vector of a particle forming the fluid from a storage unit;

calculating, with respect to a fluid model representing the fluid as a collection of particles, a force applied to each particle and a surface tension applied to each particle using the obtained position vector and velocity vector;

adding the calculated force applied to each particle and surface tension applied to each particle to the velocity vector so as to update a velocity of each particle;

calculating a shape change in the fluid using the updated velocity of each particle; and outputting the calculated shape change to an output unit, wherein $$v_i^{*,n+1} = \bar{v}_i^n - 2dt\left[\sum_j m_j\left(\frac{p_{ij}^{n+1/2}}{\rho_i^n \rho_j^n}\right)\left(\frac{L(\bar{r}_i^*) + L(\bar{r}_j^*)}{2}\right)\frac{\partial W(|\bar{r}_i^* - \bar{r}_j^*|, h)}{\partial \bar{r}_i^*}\right] -$$

$$\frac{1}{2}\sum_j m_j\left(\frac{4\mu\xi}{\rho_i \rho_j}\frac{(\bar{v}_i^n - \bar{v}_j^n)\cdot(\bar{r}_i^* - \bar{r}_j^*)}{|\bar{r}_i^* - \bar{r}_j^*|^2 + \eta^2}\right)v_{ij}^i \frac{\partial W(|\bar{r}_i^* - \bar{r}_j^*|, h)}{\partial \bar{r}_i^*} -$$

$$g\hat{y} + \frac{f_{ij}}{m_i} + \frac{f_{i,sl}}{m_i}, \quad \text{[Formula 12]}$$

is used when updating the velocity of each particle, [Formula 12] including a second term on the right side expressing a pressure gradient term, a third term on the right side expressing a viscous stress term, a fourth term on the right side expressing a gravity term, and a fifth term on the right side which is a force for preventing the distance between particles from becoming too close, to calculate the force applied to each particle, as well as a sixth term on the right side which is a surface tension, and followed by the following calculation:

$$r_i^{*,n+1} = \bar{r}_i^* + \frac{dt}{2}v_i^{*,n+1} \quad \text{[Formula 13]}$$

$$r_i^{n+1} = \begin{cases} r_i^{*,n+1} & y_i^{*,n+1} > 0 \\ r_i^{*,n+1} - \frac{y_i^{*,n+1}}{v_{i,y}^{*,n+1}}v_i^{*,n+1} & y_i^{*,n+1} \leq 0 \end{cases}, \quad \text{[Formula 14]}$$

$$v_i^{n+1} = \begin{cases} v_i^{*,n+1} & y_i^{*,n+1} > 0 \\ \left(1 - \frac{y_i^{*,n+1}}{dt v_{i,y}^{*,n+1}}\right)v_i^{*,n+1} & y_i^{*,n+1} \leq 0 \end{cases}$$

$$\rho_i^{n+1} = \rho_i^n + 2dt\sum_j \frac{m_j \rho_i^n}{\rho_j^n}\left(\frac{v_i^{s,n+1} + \bar{v}_i^{s,n}}{2} - \right. \quad \text{[Formula 15]}$$

$$\left. v_{ij}^{s,n+1/2}\right)\frac{\partial}{\partial(|\bar{r}_i^* - \bar{r}_j^*|)}W(|\bar{r}_i^* - \bar{r}_j^*|, h),$$

wherein
  a subscript expresses the number of the particle, that is,
  $r_i$, $v_i$, $\rho_i$, $p_i$ represent the position vector, velocity vector, density, and pressure of the i-th particle respectively,
  $m_j$ is the mass of the j-th particle, and
  $\xi$, $\eta$ are constants introduced to calculate a viscous term, wherein $$f_{ij} = \frac{8}{r_{min}^2}\left(1 - \left(\frac{|\bar{r}_i^* - \bar{r}_j^*|}{r_{min}}\right)^2\right)\frac{\bar{r}_i^* - \bar{r}_j^*}{|\bar{r}_i^* - \bar{r}_j^*|}$$

($r_{min}$ is a constant), wherein $$f_{k,sl} = -\frac{\partial}{\partial r_k}E_{s,p1}(r_1, r_2, \ldots, r_n) \approx \quad \text{[Formula 6]}$$

$$Q\sum_j\left[(\Gamma_g - \Gamma_s)\left(\frac{m_k}{\rho_k}\left(\frac{m_j}{\rho_j}\right)^{1-\frac{1}{d}}f_k\chi_j + \frac{m_j}{\rho_j}\left(\frac{m_k}{\rho_k}\right)^{1-\frac{1}{d}}f_j\chi_k\right) + \right.$$

-continued $$\left. \Gamma_s\left(\frac{m_k}{\rho_k}\left(\frac{m_j}{\rho_j}\right)^{1-\frac{1}{d}}f_k + \frac{m_j}{\rho_j}\left(\frac{m_k}{\rho_k}\right)^{1-\frac{1}{d}}f_j\right)\right]\frac{\partial W(|r_k - r_j|, h)}{\partial r_k} -$$

$$Q(\Gamma_g - \Gamma_s)\sum_j \frac{m_j}{\rho_j}\left(\frac{m_k}{\rho_k}\right)^{1-\frac{1}{d}}f_j\frac{\partial \chi_k}{\partial r_k}W(|r_k - r_j|)$$

is applied, and
$\chi_i = \chi_i(\bar{y}_i^*, \epsilon)$
if a plain surface of y=0 is a wall surface of a solid, wherein
  g is gravity acceleration,
  y is a unit vector in the y direction,
  h expresses an influence radius which is a radius of a spherical area in which a value of a kernel function is non-zero, and
  W is an overlap of kernel functions used in the SPH method, wherein
  $L(\bar{r}_i^*)$
  is a renormalization matrix of $$L(r_i) = \left[\sum_j \frac{m_j}{\rho_j}(r_j - r_i) \otimes \frac{\partial}{\partial r_i}W(|r_i - r_j|, h)\right]^{-1},$$

and if $$\bar{n}_{ij}^* = \left(\frac{L(\bar{r}_i^*) + L(\bar{r}_j^*)}{2}\right)^3 \frac{\bar{r}_i^* - \bar{r}_j^*}{|\bar{r}_i^* - \bar{r}_j^*|}$$

$v_i^{s,n} = \bar{v}_i^n \cdot \bar{n}_{ij}^*$
$v_j^{s,n} = \bar{v}_j^n \cdot \bar{n}_{ij}^*$,
wherein
  $p_{ij}^{n+1/2}, v_{ij}^{s,n+1/2}$
  are intermediate values of space-time determined by solving the one-dimensional Riemann problem between the particles i and j, the values being determined by a process including:
  first setting the following characteristic quantities with respect to the particles i and j:

$$q_i^{n,+} = \log(\rho_i^n) + \frac{v_i^{s,n}}{c} \quad \text{[Formula 16]}$$

$$q_i^{n,-} = \log(\rho_i^n) - \frac{v_i^{s,n}}{c} \quad \text{[Formula 17]}$$

$$q_j^{n,+} = \log(\rho_j^n) + \frac{v_j^{s,n}}{c} \quad \text{[Formula 18]}$$

$$q_j^{n,-} = \log(\rho_j^n) - \frac{v_j^{s,n}}{c}; \quad \text{[Formula 19]}$$

and
  then calculating each gradient as follows:

$$\nabla\log(\rho)|_i = \sum_k \frac{m_k}{\rho_i}(\log(\rho_k^n) - \log(\rho_i^n))L(\bar{r}_i^*)\frac{\partial W(|\bar{r}_i^* - \bar{r}_k^*|, h)}{\partial \bar{r}_i^*} \quad \text{[Formula 20]}$$

$$\nabla v|_i = \sum_k \frac{m_k}{\rho_k}L(\bar{r}_i^*)\frac{\partial W(|\bar{r}_i^* - \bar{r}_k^*|, h)}{\partial \bar{r}_i^*} \otimes (\bar{v}_k^n - \bar{v}_i^n) \quad \text{[Formula 21]}$$

-continued $$\nabla q|_i^{n,+} = \nabla \log(\rho)|_i + \frac{\nabla v|_i \bar{n}_{ij}^*}{c} \quad \text{[Formula 22]}$$

$$\nabla q|_j^{n,+} = \nabla \log(\rho)|_j + \frac{\nabla v|_j \bar{n}_{ij}^*}{c} \quad \text{[Formula 23]}$$

$$\nabla q|_i^{n,-} = \nabla \log(\rho)|_i - \frac{\nabla v|_i \bar{n}_{ij}^*}{c} \quad \text{[Formula 24]}$$

$$\nabla q|_j^{n,-} = \nabla \log(\rho)|_j - \frac{\nabla v|_j \bar{n}_{ij}^*}{c}, \quad \text{[Formula 25]}$$

and wherein
$\bar{r}_{ij}^* = \bar{r}_i^* - \bar{r}_j^*$,
$\bar{r}_{ij}^* = |\bar{r}_{ij}^*|$
and using the above quantities,
$p_{ij}^{n+1/2}, v_{ij}^{n+1/2}$
are determined as follows:

$$q_{ij}^{n+1/2,+} = q_j^{n,+} + \left(\frac{|\bar{r}_{ij}^*|}{2} - \frac{cdt}{2}\right)(\bar{r}_{ij}^* \cdot \nabla q|_j^{n,+}) \quad \text{[Formula 26]}$$

$$q_{ij}^{n+1/2,-} = q_i^{n,-} - \left(\frac{|\bar{r}_{ij}^*|}{2} + \frac{cdt}{2}\right)(\bar{r}_{ij}^* \cdot \nabla q|_i^{n,-}) \quad \text{[Formula 27]}$$

$$\rho_{ij}^{n+1/2} = \exp\left(\frac{q_{ij}^{n+1/2,+} + q_{ij}^{n+1/2,-}}{2}\right) \quad \text{[Formula 28]}$$

$$v_{ij}^{n+1/2} = c\left(\frac{q_{ij}^{n+1/2,+} - q_{ij}^{n+1/2,-}}{2}\right) \quad \text{[Formula 29]}$$

$$p_{ij}^{n+1/2} = c^2(\rho_{ij}^{n+1/2} + \rho_0). \quad \text{[Formula 30]}$$

2. The non-transitory computer-readable recording medium according to claim 1, wherein the function is for calculating the sum of the result of the calculation of the surface energy of the interface with a phase of the air, and the result of the calculation of the surface energy of the interface with a phase of other than the phase of the air.

3. The non-transitory computer-readable recording medium according to claim 1, wherein in the calculation of a shape change, the particle forming the fluid is stopped when the fluid collides against a wall surface.

4. A simulation method for suppressing behaviors including generating an unnatural velocity distribution when simulating a temporal shape change in a fluid by using a processor, the simulation method comprising:
   obtaining a position vector and a velocity vector of a particle forming the fluid from a storage unit by using the processor;
   calculating, with respect to a fluid model representing the fluid as a collection of particles, a force applied to each particle and a surface tension applied to each particle using the obtained position vector and velocity vector by using the processor;
   adding the calculated force applied to each particle and surface tension applied to each particle to the velocity vector so as to update a velocity of each particle by using the processor;
   calculating a shape change in the fluid using the updated velocity of each particle by using the processor; and
   outputting the calculated shape change to an output unit by using the processor, wherein $$v_i^{*,n+1} = v_i^n - 2dt\left[\sum_j m_j\left(\frac{p_{ij}^{n+1/2}}{\rho_i^n \rho_j^n}\right)\left(\frac{L(\bar{r}_i^*) + L(\bar{r}_j^*)}{2}\right)\frac{\partial W(|\bar{r}_i^* - \bar{r}_j^*|, h)}{\partial \bar{r}_i^*}\right] - \frac{1}{2}\sum_j m_j\left(\frac{4\mu\xi}{\rho_i\rho_j}\frac{(\bar{v}_i^n - \bar{v}_j^n)\cdot(\bar{r}_i^* - \bar{r}_j^*)}{|\bar{r}_i^* - \bar{r}_j^*|^2 + \eta^2}\right)v_{ij}^*\frac{\partial W(|\bar{r}_i^* - \bar{r}_j^*|, h)}{\partial \bar{r}_i^*} - g\hat{y} + \frac{f_{ij}}{m_i} + \frac{f_{i,s1}}{m_i}, \quad \text{[Formula 12]}$$

is used when updating the velocity of each particle, [Formula 12] including a second term on the right side expressing a pressure gradient term, a third term on the right side expressing a viscous stress term, a fourth term on the right side expressing a gravity term, and a fifth term on the right side which is a force for preventing the distance between particles from becoming too close, to calculate the force applied to each particle, as well as a sixth term on the right side which is a surface tension, and followed by the following calculation:

$$r_i^{*,n+1} = \bar{r}_i^* + \frac{dt}{2}v_i^{*,n+1} \quad \text{[Formula 13]}$$

$$r_i^{n+1} = \begin{cases} r_i^{*,n+1} & y_i^{*,n+1} > 0 \\ r_i^{*,n+1} - \frac{y_i^{*,n+1}}{v_{i,y}^{*,n+1}} v_i^{*,n+1} & y_i^{*,n+1} \leq 0 \end{cases}, \quad \text{[Formula 14]}$$

$$v_i^{n+1} = \begin{cases} v_i^{*,n+1} & y_i^{*,n+1} > 0 \\ \left(1 - \frac{y_i^{*,n+1}}{dt v_{i,y}^{*,n+1}}\right)v_i^{*,n+1} & y_i^{*,n+1} \leq 0 \end{cases}$$

$$\rho_i^{n+1} = \rho_i^n + 2dt\sum_j \frac{m_j \rho_i^n}{\rho_j^n}\left(\frac{v_i^{s,n+1} + \bar{v}_i^{s,n}}{2} - v_{ij}^{s,n+1/2}\right)\frac{\partial}{\partial(|\bar{r}_i^* - \bar{r}_j^*|)}W(|\bar{r}_i^* - \bar{r}_j^*|, h), \quad \text{[Formula 15]}$$

wherein
  a subscript expresses the number of the particle, that is,
  $r_i, v_i, \rho_i, p_i$ represent the position vector, velocity vector, density, and pressure of the i-th particle respectively,
  $m_j$ is the mass of the j-th particle, and
  $\xi, \eta$ are constants introduced to calculate a viscous term, wherein $$f_{ij} = \frac{8}{r_{min}^2}\left(1 - \left(\frac{|\bar{r}_i^* - \bar{r}_j^*|}{r_{min}}\right)^2\right)^3 \frac{\bar{r}_i^* - \bar{r}_j^*}{|\bar{r}_i^* - \bar{r}_j^*|}$$

($r_{min}$ is a constant), wherein $$f_{k,s1} = -\frac{\partial}{\partial r_k}E_{s,p1}(r_1, r_2, \ldots, r_n) \approx \quad \text{[Formula 6]}$$

$$Q\sum_j\left[(\Gamma_g - \Gamma_s)\left(\frac{m_k}{\rho_k}\left(\frac{m_j}{\rho_j}\right)^{1-\frac{1}{d}}f_k\chi_j + \frac{m_j}{\rho_j}\left(\frac{m_k}{\rho_k}\right)^{1-\frac{1}{d}}f_j\chi_k\right) + \right.$$

-continued $$\Gamma_s \left( \frac{m_k}{\rho_k} \left(\frac{m_j}{\rho_k}\right)^{1-\frac{1}{d}} f_k + \frac{m_j}{\rho_j} \left(\frac{m_k}{\rho_k}\right)^{1-\frac{1}{d}} f_j \right) \right]$$

$$\frac{\partial W(|r_k - r_j|, h)}{\partial r_k} -$$

$$Q(\Gamma_g - \Gamma_s) \sum_j \frac{m_j}{\rho_j} \left(\frac{m_k}{\rho_k}\right)^{1-\frac{1}{d}} f_j \frac{\partial \chi_k}{\partial r_k} W(|r_k - r_j|)$$

is applied, and
$\chi_i = \chi_i(\bar{y}_i^*:\epsilon)$
if a plain surface of v=0 is a wall surface of a solid, wherein
g is gravity acceleration,
y is a unit vector in the y direction,
h expresses an influence radius which is a radius of a spherical area in which a value of a kernel function is non-zero, and
W is an overlap of kernel functions used in the SPH method, wherein
$L(\bar{r}_i^*)$
is a renormalization matrix of $$L(r_i) = \left[ \sum_j \frac{m_j}{\rho_j} (r_j - r_i) \otimes \frac{\partial}{\partial r_i} W(|r_i - r_j|, h) \right]^{-1},$$

and if $$\bar{n}_{ij}^* = \left( \frac{L(\bar{r}_i^*) + L(\bar{r}_j^*)}{2} \right) \frac{\bar{r}_i^* - \bar{r}_j^*}{|\bar{r}_i^* - \bar{r}_j^*|}$$

$v_i^{s,n} = \bar{v}_i^n \cdot \bar{n}_{ij}^*$
$v_j^{s,n} = \bar{v}_j^n \cdot \bar{n}_{ij}^*$,
wherein
$p_{ij}^{n+1/2}, v_{ij}^{s,n+1/2}$
are intermediate values of space-time determined by solving the one-dimensional Riemann problem between the particles i and j, the values being determined by a process including:
first setting the following characteristic quantities with respect to the particles i and j:

$$q_i^{n,+} = \log(\rho_i^n) + \frac{v_i^{s,n}}{c}$$ [Formula 16]

$$q_i^{n,-} = \log(\rho_i^n) - \frac{v_i^{s,n}}{c}$$ [Formula 17]

$$q_j^{n,+} = \log(\rho_j^n) + \frac{v_j^{s,n}}{c}$$ [Formula 18]

$$q_j^{n,-} = \log(\rho_j^n) - \frac{v_j^{s,n}}{c};$$ [Formula 19]

and
then calculating each gradient as follows:

$$\nabla \log(\rho)|_i =$$ [Formula 20]
$$\sum_k \frac{m_k}{\rho_i} (\log(\rho_k^n) - \log(\rho_i^n)) L(\bar{r}_i^*) \frac{\partial W(|\bar{r}_i^* - \bar{r}_k^*|, h)}{\partial \bar{r}_i^*}$$

$$\nabla v|_i = \sum_k \frac{m_k}{\rho_k} L(\bar{r}_i^*) \frac{\partial W(|\bar{r}_i^* - \bar{r}_k^*|, h)}{\partial \bar{r}_i^*} \otimes (\bar{v}_k^n - \bar{v}_i^n)$$ [Formula 21]

$$\nabla q|_i^{n,+} = \nabla \log(\rho)|_i + \frac{\nabla v|_i \bar{n}_{ij}^*}{c}$$ [Formula 22]

$$\nabla q|_j^{n,+} = \nabla \log(\rho)|_j + \frac{\nabla v|_j \bar{n}_{ij}^*}{c}$$ [Formula 23]

$$\nabla q|_i^{n,-} = \nabla \log(\rho)|_i - \frac{\nabla v|_i \bar{n}_{ij}^*}{c}$$ [Formula 24]

$$\nabla q|_j^{n,-} = \nabla \log(\rho)|_j - \frac{\nabla v|_j \bar{n}_{ij}^*}{c},$$ [Formula 25]

and wherein
$\bar{r}_{ij}^* = \bar{r}_i^* - \bar{r}_j^*$,
$r_{ij}^* = |\bar{r}_{ij}^*|$
and using the above quantities,
$p_{ij}^{n+1/2}, v_{ij}^{s,n+1/2}$
are determined as follows:

$$q_{ij}^{n+1/2,+} = q_i^{n,+} + \left( \frac{|\bar{r}_{ij}^*|}{2} - \frac{cdt}{2} \right) (\bar{r}_{ij}^* \cdot \nabla q|_j^{n,+})$$ [Formula 26]

$$q_{ij}^{n+1/2,-} = q_i^{n,-} - \left( \frac{|\bar{r}_{ij}^*|}{2} + \frac{cdt}{2} \right) (\bar{r}_{ij}^* \cdot \nabla q|_i^{n,-})$$ [Formula 27]

$$\rho_{ij}^{n+1/2} = \exp\left( \frac{q_{ij}^{n+1/2,+} + q_{ij}^{n+1/2,-}}{2} \right)$$ [Formula 28]

$$v_{ij}^{n+1/2} = c \left( \frac{q_{ij}^{n+1/2,+} - q_{ij}^{n+1/2,-}}{2} \right)$$ [Formula 29]

$$p_{ij}^{n+1/2} = c^2 (\rho_{ij}^{n+1/2} + \rho_0).$$ [Formula 30]

5. A simulation device for suppressing behaviors including generating an unnatural velocity distribution when simulating a temporal shape change in a fluid, the simulation device comprising:
a processor which performs a process including:
obtaining a position vector and a velocity vector of a particle forming the fluid from a storage unit,
calculating, with respect to a fluid model representing the fluid as a collection of particles, a force applied to each particle and a surface tension applied to each particle using the obtained position vector and velocity vector;
adding the calculated force applied to each particle and surface tension applied to each particle to the velocity vector so as to update a velocity of each particle;
calculating a shape change in the fluid using the updated velocity of each particle; and
an output unit configured to output the calculated shape change, wherein $$v_i^{*,n+1} = \bar{v}_i^n -$$ [Formula 12]
$$2dt \left[ \sum_j m_j \left( \frac{p_{ij}^{n+1/2}}{\rho_i^n \rho_j^n} \right) \left( \frac{L(\bar{r}_i^*) + L(\bar{r}_j^*)}{2} \right) \frac{\partial W(|\bar{r}_i^* - \bar{r}_j^*|, h)}{\partial r_i^*} \right] -$$

-continued $$\frac{1}{2}\sum_j m_j\left(\frac{4\mu\xi}{\rho_i\rho_j}\frac{(\bar{v}_i^n-\bar{v}_j^n)\cdot(\bar{r}_i^*-\bar{r}_j^*)}{|\bar{r}_i^*-\bar{r}_j^*|^2+\eta^2}\right)v_{ij}\frac{\partial W(|\bar{r}_i^*-\bar{r}_j^*|,h)}{\partial \bar{r}_i^*}-$$

$$g\hat{y}+\frac{f_{ij}}{m_i}+\frac{f_{i,s1}}{m_i},$$

is used when updating the velocity of each particle, [Formula 12] including a second term on the right side expressing a pressure gradient term, a third term on the right side expressing a viscous stress term, a fourth term on the right side expressing a gravity term, and a fifth term on the right side which is a force for preventing the distance between particles from becoming too close, to calculate the force applied to each particle, as well as a sixth term on the right side which is a surface tension, and followed by the following calculation:

$$r_i^{*,n+1} = \bar{r}_i^* + \frac{dt}{2}v_i^{*,n+1} \quad \text{[Formula 13]}$$

$$r_i^{n+1} = \begin{cases} r_i^{*,n+1} & y_i^{*,n+1} > 0 \\ r_i^{*,n+1} - \frac{y_i^{*,n+1}}{v_{i,y}^{*,n+1}} & y_i^{*,n+1} \le 0, \end{cases} \quad v_i^{n+1} = \quad \text{[Formula 14]}$$

$$\begin{cases} v_i^{*,n+1} & y_i^{*,n+1} > 0 \\ \left(1-\frac{y_i^{*,n+1}}{dt v_{i,y}^{*,n+1}}\right)v_i^{*,n+1} & y_i^{*,n+1} \le 0 \end{cases}$$

$$\rho_i^{n+1} = \rho_i^n + 2dt\sum_j \frac{m_j\rho_i^n}{\rho_j^n}\left(\frac{v_i^{s,n+1}+\bar{v}_i^{s,n}}{2}-v_{ij}^{s,n+1/2}\right) \quad \text{[Formula 15]}$$

$$\frac{\partial}{\partial(|\bar{r}_i^*-\bar{r}_j^*|)}W(|\bar{r}_i^*-\bar{r}_j^*|,h),$$

wherein
  a subscript expresses the number of the particle, that is,
$r_i, v_i, \rho_i, p_i$ represent the position vector, velocity vector, density, and pressure of the i-th particle respectively,
$m_j$ is the mass of the j-th particle, and
$\xi, \eta$ are constants introduced to calculate a viscous term, wherein $$f_{ij} = \frac{8}{r_{min}^2}\left(1-\left(\frac{|\bar{r}_i^*-\bar{r}_j^*|}{r_{min}}\right)^2\right)^3\frac{\bar{r}_i^*-\bar{r}_j^*}{|\bar{r}_i^*-\bar{r}_j^*|}$$

($r_{min}$ is a constant), wherein $$f_{k,s1} = -\frac{\partial}{\partial r_k}E_{s,p1}(r_1,r_2,\ldots,r_n) \approx \quad \text{[Formula 6]}$$

$$Q\sum_j\left[(\Gamma_g-\Gamma_s)\left(\frac{m_k}{\rho_k}\left(\frac{m_j}{\rho_j}\right)^{1-\frac{1}{d}}f_k\chi_j+\frac{m_j}{\rho_j}\left(\frac{m_k}{\rho_k}\right)^{1-\frac{1}{d}}f_j\chi_k\right)+\right.$$

$$\left.\Gamma_s\left(\frac{m_k}{\rho_k}\left(\frac{m_j}{\rho_j}\right)^{1-\frac{1}{d}}f_k+\frac{m_j}{\rho_j}\left(\frac{m_k}{\rho_k}\right)^{1-\frac{1}{d}}f_j\right)\right]$$

$$\frac{\partial W(|r_k-r_j|,h)}{\partial r_k}-$$

-continued $$Q(\Gamma_g-\Gamma_s)\sum_j\frac{m_j}{\rho_j}\left(\frac{m_k}{\rho_k}\right)^{1-\frac{1}{d}}f_j\frac{\partial\chi_k}{\partial r_k}W(|r_k-r_j|)$$

is applied, and
$\chi_i=\chi_i(\bar{y}_i^*,\epsilon)$
if a plain surface of y=0 is a wall surface of a solid, wherein
  g is gravity acceleration,
  y is a unit vector in the y direction,
  h expresses an influence radius which is a radius of a spherical area in which a value of a kernel function is non-zero, and
  W is an overlap of kernel functions used in the SPH method,
wherein
  $L(\bar{r}_i^*)$
  is a renormalization matrix of $$L(r_i) = \left[\sum_j\frac{m_j}{\rho_j}(r_j-r_i)\otimes\frac{\partial}{\partial r_i}W(|r_i-r_j|,h)\right]^{-1},$$

and if $$\bar{n}_{ij}^* = \left(\frac{L(\bar{r}_i^*)+L(\bar{r}_j^*)}{2}\right)\frac{\bar{r}_i^*-\bar{r}_j^*}{|\bar{r}_i^*-\bar{r}_j^*|}$$

$v_i^{s,n} = \bar{v}_i^n\cdot\bar{n}_{ij}^*$,
$v_j^{s,n} = \bar{v}_j^n\cdot\bar{n}_{ij}^*$,
  wherein
    $p_{ij}^{n+1/2}, v_{ij}^{s,n+1/2}$
  are intermediate values of space-time determined by solving the one-dimensional Riemann problem between the particles i and j, the values being determined by a process including:
    first setting the following characteristic quantities with respect to the particles i and j:

$$q_i^{n,+} = \log(\rho_i^n) + \frac{v_i^{s,n}}{c} \quad \text{[Formula 16]}$$

$$q_i^{n,-} = \log(\rho_i^n) - \frac{v_i^{s,n}}{c} \quad \text{[Formula 17]}$$

$$q_j^{n,+} = \log(\rho_j^n) + \frac{v_j^{s,n}}{c} \quad \text{[Formula 18]}$$

$$q_j^{n,-} = \log(\rho_j^n) - \frac{v_j^{s,n}}{c}; \quad \text{[Formula 19]}$$

and
then calculating each gradient as follows:

$$\nabla\log(\rho)|_i = \quad \text{[Formula 20]}$$
$$\sum_k\frac{m_k}{\rho_i}(\log(\rho_k^n)-\log(\rho_i^n))L(\bar{r}_i^*)\frac{\partial W(|\bar{r}_i^*-\bar{r}_k^*|,h)}{\partial \bar{r}_i^*}$$

$$\nabla v|_i = \sum_k\frac{m_k}{\rho_k}L(\bar{r}_i^*)\frac{\partial W(|\bar{r}_i^*-\bar{r}_k^*|,h)}{\partial \bar{r}_i^*}\otimes(\bar{v}_k^n-\bar{v}_i^n) \quad \text{[Formula 21]}$$

$$\nabla q_i^{n,+} = \nabla\log(\rho)|_i + \frac{\nabla v|_i\bar{n}_{ij}^*}{c} \quad \text{[Formula 22]}$$

-continued $$\nabla q|_j^{n,+} = \nabla \log(\rho)|_j + \frac{\nabla v|_j \bar{n}_{ij}^*}{c}$$ [Formula 23]

$$\nabla q|_i^{n,-} = \nabla \log(\rho)|_i - \frac{\nabla v|_i \bar{n}_{ij}^*}{c}$$ [Formula 24]

$$\nabla q|_j^{n,-} = \nabla \log(\rho)|_j - \frac{\nabla v|_j \bar{n}_{ij}^*}{c},$$ [Formula 25]

and wherein
$\bar{r}_{ij}^* = \bar{r}_i^* - \bar{r}_j^*$,
$r_{ij}^* = |\bar{r}_{ij}^*|$
and using the above quantities,
$p_{ij}^{n+1/2}, v_{ij}^{s,n+1/2}$
are determined as follows:

$$q_{ij}^{n+1/2,+} = q_j^{n,+} + \left(\frac{|\bar{r}_{ij}^*|}{2} - \frac{cdt}{2}\right)(\bar{r}_{ij}^* \cdot \nabla q|_j^{n,+})$$ [Formula 26]

$$q_{ij}^{n+1/2,-} = q_i^{n,+} - \left(\frac{|\bar{r}_{ij}^*|}{2} + \frac{cdt}{2}\right)(\bar{r}_{ij}^* \cdot \nabla q|_i^{n,-})$$ [Formula 27]

$$\rho_{ij}^{n+1/2} = \exp\left(\frac{q_{ij}^{n+1/2,+} + q_{ij}^{n+1/2,-}}{2}\right)$$ [Formula 28]

$$v_{ij}^{n+1/2} = c\left(\frac{q_{ij}^{n+1/2,+} - q_{ij}^{n+1/2,-}}{2}\right)$$ [Formula 29]

$$p_{ij}^{n+1/2} = c^2(\rho_{ij}^{n+1/2} + \rho_0).$$ [Formula 30]

\* \* \* \* \*